US010532060B2

(12) United States Patent
Wester et al.

(10) Patent No.: US 10,532,060 B2
(45) Date of Patent: Jan. 14, 2020

(54) SERUM CHOLESTEROL LOWERING EDIBLE PRODUCT

(71) Applicant: RAISIO NUTRITION LTD, Raisio (FI)

(72) Inventors: Ingmar Wester, Raisio (FI); Paivi Kuusisto, Raisio (FI); Jouni Reijo Kalevi Niemela, Raisio (FI); Tuula Forbom, Raisio (FI); Kurt I. Draget, Raisio (FI); Andrzej Siwek, Raisio (FI); Kamilla Lundhaug, Raisio (FI); Jan Erik Olsen, Raisio (FI)

(73) Assignee: Raisio Nutrition Ltd., Raisio (FI)

( * ) Notice: Subject to any disclaimer, the term of this patent is extended or adjusted under 35 U.S.C. 154(b) by 0 days.

(21) Appl. No.: 15/120,016

(22) PCT Filed: Mar. 3, 2015

(86) PCT No.: PCT/EP2015/000476
§ 371 (c)(1),
(2) Date: Aug. 18, 2016

(87) PCT Pub. No.: WO2015/131995
PCT Pub. Date: Sep. 11, 2015

(65) Prior Publication Data
US 2017/0065616 A1 Mar. 9, 2017

(30) Foreign Application Priority Data

Mar. 3, 2014 (EP) .................................. 14000748
May 26, 2014 (EP) .................................. 14001830
Sep. 19, 2014 (WO) ................. PCT/EP2014/002551

(51) Int. Cl.
*A61K 31/575* (2006.01)
*A23L 29/10* (2016.01)
*A23L 33/11* (2016.01)
*A23P 20/00* (2016.01)
*A61K 47/10* (2017.01)
*A61K 47/26* (2006.01)
*A61K 47/42* (2017.01)
*A61K 47/44* (2017.01)
*A61K 9/06* (2006.01)
*A61K 9/107* (2006.01)

(52) U.S. Cl.
CPC ............ *A61K 31/575* (2013.01); *A23L 29/10* (2016.08); *A23L 33/11* (2016.08); *A23P 20/00* (2016.08); *A61K 9/06* (2013.01); *A61K 9/107* (2013.01); *A61K 47/10* (2013.01); *A61K 47/26* (2013.01); *A61K 47/42* (2013.01); *A61K 47/44* (2013.01); *A23V 2002/00* (2013.01)

(58) Field of Classification Search
CPC ........ A61K 31/575; A61K 9/06; A61K 9/107; A61K 47/10; A61K 47/26; A61K 47/42; A61K 47/44; A23V 2002/00
See application file for complete search history.

(56) References Cited

U.S. PATENT DOCUMENTS

| 6,174,560 B1 | 1/2001 | Miettenen et al. |
| 6,491,952 B1 | 12/2002 | Sjoberg |
| 2003/0044449 A1 | 3/2003 | Miyanishi et al. |
| 2007/0141224 A1* | 6/2007 | Zawistowski .......... A23D 7/001 426/611 |
| 2008/0089978 A1 | 4/2008 | Grigg et al. |
| 2008/0187645 A1* | 8/2008 | Ekblom .............. A23D 7/0056 426/602 |
| 2008/0220051 A1 | 9/2008 | Horlacher et al. |
| 2009/0130211 A1* | 5/2009 | Gamay ................. A23L 33/175 424/484 |
| 2009/0238866 A1 | 9/2009 | Haug et al. |
| 2012/0308710 A1 | 12/2012 | Beck et al. |
| 2012/0308711 A1 | 12/2012 | Schwaier et al. |

FOREIGN PATENT DOCUMENTS

| CA | 1289074 C | 9/1991 |
| CN | 102415465 A | 4/2012 |
| DE | 102005039835 A1 | 3/2007 |
| JP | H09220464 A | 8/1997 |
| JP | 2001000117 A | 1/2001 |
| JP | 2013247913 A | 12/2013 |
| WO | WO-9742830 A1 | 11/1997 |
| WO | 98/19556 A1 | 5/1998 |
| WO | WO-0041491 A2 | 7/2000 |
| WO | WO-02065859 A1 | 8/2002 |
| WO | WO-2006037847 A1 | 4/2006 |
| WO | 2007/085840 A1 | 8/2007 |
| WO | WO-2009068651 A1 | 6/2009 |
| WO | 2010/041017 A1 | 4/2010 |
| WO | WO-2011095305 A1 | 8/2011 |
| WO | WO-2012046066 A1 | 4/2012 |

OTHER PUBLICATIONS

International Search Report regarding Application No. PCT/EP2015/000476, ISA/EP, Rijswijk, NL dated May 29, 2015.
Written Opinion regarding Application No. PCT/EP2015/000476, dated May 29, 2015.
Arjen Bot et al: 11 Structuring in 1-59-sitosterol-oryzanol-based emulsion gels during various stages of a temperature cycle. Food Hydrocolloi DS. Elsevier BV. NL. vol. 25. No. 4. Jul. 28, 2010 (Jul. 28, 2010). pp. 639-646.
Argen Bot et al; Structuring in B-sitosterol + Y-oryzanol-based emulsion gels during various stages of a temperature cycle; Food Hydrocolloids 25 (2011) 639-646.

* cited by examiner

*Primary Examiner* — Doan T Phan
(74) *Attorney, Agent, or Firm* — Harness, Dickey & Pierce, P.L.C.

(57) ABSTRACT

The present invention relates to a serum LDL cholesterol lowering edible product containing plant sterol ester and/or plant stanol ester, and especially to a dietary supplement product.

17 Claims, No Drawings

SERUM CHOLESTEROL LOWERING EDIBLE PRODUCT

CROSS REFERENCE TO RELATED APPLICATIONS

This application is a U.S. National Phase under 35 U.S.C. 371 of International Application No. PCT/EP2015/000476, filed Mar. 3, 2015, and published as WO 2015/131995 on Sep. 11, 2015. This application claims the benefit of and priority to European Patent Applications 14000748.5, filed Mar. 3, 2014; 14001830.0, filed May 26, 2014 and PCT/EP2014/002551, filed Sep. 19, 2014. The entire disclosures of the above applications are incorporated herein by reference.

FIELD OF THE INVENTION

The present invention relates to an edible product having serum LDL cholesterol lowering effect, and especially to an edible product based on plant sterol ester and/or plant stanol ester. Typically the edible product is a dietary supplement product.

BACKGROUND OF THE INVENTION

Cardiovascular disease is counted among the most common diseases in Western countries and its occurrence is further increasing. The most important individual risk factor is elevated serum LDL cholesterol level, and therefore, lowering of the blood concentrations of LDL cholesterol is the most effective single measure regarding both prevention and effective treatment of cardiovascular disease.

The most important drugs for reduction of cholesterol levels are the statins, which primarily function by inhibiting the synthesis of cholesterol in the liver. The most common side effects of the statins are gastrointestinal. Other less common side effects include headache, dizziness, rash, and sleep disturbances. In addition, statins may cause both liver damage and muscle disorders, and they have been reported to increase the risk of type II diabetes.

As an alternative to drugs, or in addition to them, also life style changes can reduce the risk of cardiovascular diseases. In particular increasing physical exercise and/or adopting a low-fat or low-cholesterol diet is beneficial. Another nutritional way to reduce the serum LDL cholesterol levels is to use cholesterol lowering ingredients in functional foods that can be consumed as part of a conventional diet. This alternative has been greatly welcomed by consumers.

Foods, such as margarine-type spreads, drinkable and spoonable yoghurts, with added plant sterols and/or plant stanols for effective serum LDL cholesterol lowering are popular in the market place, especially in the European markets. Both in USA and in the EU markets food and dietary supplement products with added plant sterols and/or plant stanols can be marketed with approved coronary heart disease risk reduction health claims due to the serum LDL cholesterol lowering effect, provided that the products fulfil set conditions for use of such health claims. The success of commercial plant sterol and/or plant stanol products is dependent on the possibility to market the products with strong health claims.

In EU the product needs to deliver 1.5-2.4 g equivalents of plant sterols and/or plant stanols in order to bear such a coronary heart disease risk reduction health claim. In USA the latest provision of FDA states that the product needs to deliver at least 0.5 g equivalents of plant sterols and/or plant stanols per Reference Amount Customarily Consumed (RACC) for a total daily intake of 2 g plant sterols and/or plant stanols in order to bear the disease risk reduction health claim. The daily needed 2 g of plant sterols and/or plant stanols can be delivered in 1-4 servings of the food or the dietary supplement.

The current popular plant sterol ester and/or plant stanol ester based foods are products that need continuous refrigeration. However, many consumers would prefer to have their daily dose of plant sterols and/or plant stanols available in a product that can be carried along wherever they go, e.g. as a dietary supplement.

Dietary supplements based on esterified plant sterols and/or plant stanols are currently marketed mainly as so-called soft gelatin capsules. However one problem with this type of product is that the size of the soft gelatin capsule is big, causing problems with the swallowing of it. Such soft gelatin capsules typically deliver about 1 g plant sterol ester and/or plant stanol ester contained in each soft gelatin capsules. Usually the recommended amount of plant sterols and/or plant stanols is 2 g/day, which means that the daily minimum required amount of plant sterol ester and/or plant stanol ester is about 3.4 g. This means that the consumer has to swallow several big soft gelatin capsules per day to obtain the daily recommended amount of plant sterol and/or plant stanol in esterified form. Many consumers have difficulties in swallowing such big capsules. Furthermore the swallowing of such capsules involves simultaneous drinking of water or some other liquid and the capsules are therefore not so convenient to use.

Dietary supplements based on free plant sterols and/or plant stanols are usually compressed tablets. These are usually smaller than the soft gelatin capsules, but liquid is usually required in order to swallow the tablets. However, people with dysphagia may have difficulties in swallowing even smaller sized tablets.

Thus there is a need for a new type of portable plant sterol ester and/or plant stanol ester edible products, such as dietary supplement products. Such products should preferably be easy to consume and be portable with the possibility of being stored at room temperatures and still have long enough shelf life in order to be commercially viable. They should also preferably have good taste. Furthermore such a product should preferably deliver the daily minimum amount of plant sterols and/or plant stanols needed to fulfil the provisions of the cholesterol lowering health claims in various jurisdictions.

It would be advantageous to have a portable edible product, such as a dietary supplement product with a high plant sterol ester and/or plant stanol ester content that can be stored at room temperatures. Furthermore, such an edible product should be easy to consume with limited or no problems in swallowing and it should be possible to consume it without simultaneous consumption of any liquid. Furthermore, such an edible product preferably has low energy content. Good organoleptic properties are desirable. The formulation of the product should preferably also be such that the serum LDL cholesterol lowering effect of the plant sterol and/or plant stanol is good. The current invention satisfies these needs and provides a new type of edible product (such as a dietary supplement product) containing plant sterol ester and/or plant stanol ester.

BRIEF DESCRIPTION OF THE INVENTION

The present invention is directed to a gelled emulsion comprising plant sterol ester and/or plant stanol ester in an amount of at least 20% by weight, gelling agent in an amount of at most 15% by weight, and water in an amount of 3.0-35% by weight.

The present invention is further directed to an edible product, comprising the gelled emulsion as defined above.

The present invention is further directed to a blister comprising the gelled emulsion or the edible product.

The present invention is further directed to methods for preparing the above defined gelled emulsion and the edible product.

DETAILED DESCRIPTION OF THE INVENTION

It is thus an object of the present invention to provide a gelled emulsion which comprises plant sterol ester and/or plant stanol ester, gelling agent and water. It is also an object of the present invention to provide an edible product (such as a dietary supplement product) which comprises the gelled emulsion containing plant sterol ester and/or plant stanol ester, gelling agent and water. The gelled emulsion and the edible product are preferably aimed for lowering serum LDL cholesterol level.

It has surprisingly been found that a portable and easy to consume edible product (such as a dietary supplement product) that has good organoleptic properties and that can be stored at room temperatures and still retains its good quality and that has a high content of plant sterol ester and/or plant stanol ester can be prepared as a gelled emulsion. Preferably the product has low energy content. By using specific amounts of the plant sterol ester and/or plant stanol ester, gelling agent and water, gelled emulsions having high plant sterol ester and/or plant stanol ester content and good organoleptic properties can be obtained. By having the specific amounts of plant sterol ester and/or plant stanol ester, gelling agent and water, gelled emulsions with good texture and mouthfeel can be prepared. The mouthfeel and the surface of the gelled emulsion are not oily. Despite the high concentration of plant sterol ester and/or plant stanol ester, the gelled emulsion retains the plant sterol ester and/or plant stanol ester in the gel matrix. This is surprising, as corresponding products could not be produced by using free plant sterols and/or plant stanols instead of plant sterol ester and/or plant stanol ester. It was also surprisingly noticed that it is preferred to have a weight ratio of plant sterol ester and/or plant stanol ester to gelling agent that is at least 6.0. Preferably the gelled emulsion is a solid gelled emulsion. It is suitably used as such (i.e. uncoated) as an edible product. Most preferably the edible product (e.g. a dietary supplement product) is (i.e. consists of) a dose unit of the gelled emulsion that has been enclosed in a package. The edible product comprising the gelled emulsion (e.g. a dietary supplement product) can preferably be packed in blisters, most preferably in an aluminium blister for excellent water retaining and bather properties. The uncoated edible product (i.e. the gelled emulsion) is preferably packed as individual dose units in blisters. Alternatively, the gelled emulsion may be coated with a chewable coating or a coating that melts in the mouth. After coating the edible product may be packed as individual dose units or several dose units in the same package.

One advantage of the edible product, such as a dietary supplement product, of the present invention is the use of esterified plant sterols and/or plant stanols (i.e. plant sterol ester and/or plant stanol ester) in high concentrations in the edible product and that the product still has good organoleptic properties. The invention cannot be applied to the use of free plant sterols and/or plant stanol instead of the esterified plant sterols and/or plant stanols. The edible product is portable. This means it can easily be carried along. The edible product can be stored at room temperatures. This means that it still retains its good quality (i.e. organoleptic and microbiological quality) when stored for prolonged time at room temperatures. Thus, the edible product does not require refrigeration. The edible product is preferably a dietary supplement product. The edible product comprises a gelled emulsion, which is preferably solid at room temperatures, but has a soft and chewable texture with good taste. The edible product is not spreadable. The edible product is chewable. Thus the consumer does not need to swallow capsules or tablets, but can easily chew the edible product. Further, the edible product can be consumed without necessary ingesting liquid at the same time. The edible product is therefore easy to consume. The edible product preferably has a low energy content.

Plant sterol ester and/or plant stanol ester are solid, semi-solid or liquid at room temperatures and typically result in an unpleasant fatty coating of the mouth, especially of the back roof of the mouth, when ingested as such. Surprisingly the mouthfeel of the gelled emulsion according to this invention is not oily, nor fatty, and further it does not cause any unpleasant fatty coating in the back roof of the mouth upon ingestion, despite its high plant sterol ester and/or plant stanol ester content. The mouthfeel is not gummy or sticky either and the gelled emulsion does not get caught onto the teeth.

The gelled emulsion is chewable. The gelled emulsion is preferably solid at room temperatures (e.g. 22° C.), not pourable, and even when removed from its package (e.g. when packed in aluminium blisters) and stored at room temperatures the gelled emulsion still retains its physical state and form.

Despite the high content of plant sterol ester and/or plant stanol ester the preparation of the gelled emulsion does not require high concentrations of the gelling agent or gelling agent mixture. The physical properties of the emulsion, such as stability and viscosity of the emulsion at temperatures where the emulsification and the further processing take place, are such that it enables the production and packaging.

The production process of the edible product, e.g. a dietary supplement product can, but does not preferably include coating of the gelled emulsion. Preferably the production process does not include any drying step. The edible product can be stored at room temperature, especially when packed in aluminium blisters. Therefore the edible product has a long shelf life at room temperature. The shelf life is from at least 6 months up to several years.

Thus, the present invention is directed to an edible product, preferably a dietary supplement product, preferably a serum LDL cholesterol lowering dietary supplement product, which comprises a gelled emulsion containing plant sterol ester and/or plant stanol ester in an amount of at least 20% by weight, gelling agent in an amount of at most 15% by weight, and water in an amount of 3.0-35% by weight.

The present invention is also directed to the above defined gelled emulsion.

The present invention is further directed to a blister comprising the gelled emulsion or the edible product.

The present invention is further directed to the gelled emulsion and to the edible product, preferably a dietary supplement product, for use as a medicament. By medicament is here meant a substance that is physiologically active in preventing or alleviating a disease or a risk factor of a disease. The gelled emulsion and the edible product are suitable e.g. for treating or alleviating asthma, Alzheimer's disease and/or for reducing the risk of cardiovascular disease.

The present invention is further directed to the gelled emulsion and to the edible product, preferably a dietary supplement product, for lowering serum LDL cholesterol level.

By "dietary supplement product" is in this disclosure meant edible products that are not presented or marketed as conventional food products but to supplement the diet with plant sterol ester and/or plant stanol ester with preferably the aim of reducing serum LDL cholesterol concentrations. In this disclosure, the term "dietary supplement" also covers edible products that fulfil the aforementioned definition, but can be presented or marketed in some countries for similar purposes such as "a medical food" or "a medical device". The dietary supplement products do not substitute for meals, snacks or for a daily diet. The edible product, e.g. a dietary supplement product, of the present invention is preferably a low-energy, gelled water-in-oil emulsion that is solid at room temperatures and more preferably it is uncoated.

By "emulsion" is in this disclosure meant a mixture of an aqueous phase and a lipid phase containing plant sterol ester and/or plant stanol ester, wherein both phases are in liquid form at the temperature of the emulsifying process, and wherein one phase is evenly dispersed as small droplets throughout the other phase. The emulsion is preferably an oil-in-water (O/W) emulsion, or if desired, it can also be more than biphasic (e.g. a double emulsion). By "oil-in-water (O/W) emulsion" is meant emulsions in which lipids are present as the dispersed phase and water as the continuous phase.

By "gelled emulsion" is in this disclosure meant an emulsion which contains plant sterol ester and/or plant stanol ester and a gelled aqueous phase containing gelling agent. In the gelled aqueous phase, the gelling agent has formed a rigid three dimensional network that traps or immobilises the water within the interstices. The gelled emulsion is thus a gel. Preferably the gelled emulsion is an oil-in-water-type emulsion. The plant sterol ester and/or plant stanol ester is emulsified with the aqueous phase containing gelling agent, preferably at a temperature of at least 40° C. Gelation of the gelling agent in the aqueous phase then stabilizes the emulsion, i.e. a "gelled emulsion" is formed. Gelation involves association of the gelling agent molecules with each other to form a three dimensional network, i.e. a gel. The process of gelling is complex and affected by the nature and concentrations of different components in the emulsion, as well as on the processing conditions. Gelation happens e.g. upon cooling or with the aid of ions, e.g. Ca ions. Preferably the gelation happens upon cooling. Gel forming capability is dependent not only on the nature of the gelling agent, but also depends on other factors such as the concentration of the gelling agent, water concentration and plant sterol ester and/or plant stanol ester concentration. The plant sterol ester and/or plant stanol ester phase is thus dispersed throughout the gel matrix, i.e. within the network of gelling agent molecules and immobilised water. The plant sterol ester and/or plant stanol ester is in liquid, semi-solid and/or solid state, preferably in semi-solid and/or solid state, in the gelled emulsion at room temperatures. The aqueous phase is in gelled form at room temperature (e.g. 22° C.). The plant sterol ester and/or plant stanol ester phase may or may not chemically interact with the gel matrix. The gelled emulsion of the present invention is chewable. The gelled emulsion is not spreadable. The gelled emulsion is not a powder. The gelled emulsion of the present invention is preferably solid at room temperatures (e.g. 22° C.). Most preferably the gelled emulsion is a solid gelled emulsion (at 22° C.).

By "solid gelled emulsion" is in this disclosure meant a gelled emulsion of the present invention which has a solid appearance and retains its structure at room temperature (e.g. 22° C.). The solid gelled emulsion is not pourable at room temperatures. With the term solid gelled emulsion is meant that the gelled emulsion retains its form (i.e. shape, which means it retains its three-dimensional form) at room temperature. This means that when it is released from its blister or other mould the form is retained i.e. even when it is stored as such without any coating or mould the form is retained. The solid gelled emulsion therefore has a solid appearance at 20° C., preferably at 22° C., more preferably at 25° C., and most preferably at 30° C. Practically, solid gelled emulsion means that the product is solid enough for one to pick it with one's fingers from the package. When the temperature is raised above 30° C., the solid gelled emulsion is preferably softened. More preferably the solid gelled emulsion is softened at temperatures around or higher than 35° C. Preferably the gelling of the aqueous phase of the solid gelled emulsion is thermally reversible, i.e. the gel structure is broken when temperature is raised to or above the gel melting temperature.

The gelled emulsion and the edible product (such as a dietary supplement product) according to the current invention contains plant sterol ester and/or plant stanol ester. As used in this disclosure, the term "plant sterol ester and/or plant stanol ester" refers to plant sterols and/or plant stanols in esterified form. The term "plant sterols" means 4-desmethyl sterols and 4-monomethyl sterols and the term "plant stanols" means 4-desmethyl stanols and 4-monomethyl stanols. Typical 4-desmethyl sterols are sitosterol, campesterol, stigmasterol, brassicasterol, 22-dehydro-brassicasterol and δ5-avenasterol. Typical stanols are sitostanol, campestanol and their C24-epimers. The term "plant sterols and/or plant stanols" means all possible mixtures of named sterols and/or stanols as well as any individual sterol and/or stanol.

In this invention plant sterols and/or plant stanols are esterified with a carboxylic acid or with a blend of carboxylic acids and are called "plant sterol ester and/or plant stanol ester". Examples of suitable carboxylic acids are fatty acids, which are preferred carboxylic acids according to this invention. The fatty acids are aliphatic, have 4-24 carbon atoms, and are saturated, monounsaturated or polyunsaturated. Preferably the plant sterols and/or plant stanols are thus esterified with fatty acids (so called plant sterol fatty acid ester and/or plant stanol fatty acid ester), more preferably with vegetable oil based fatty acids. Preferred are fatty acids of liquid vegetable oils, such as rapeseed oil, soybean oil, sunflower oil and corn oil.

Most preferred are plant stanol fatty acid esters. Therefore, "the plant sterol ester and/or plant stanol ester" comprises preferably plant stanol ester in an amount of at least 10%, more preferably at least 50%, still more preferably at least 70% and most preferably at least 90% by weight. Preferably plant sterol ester and/or plant stanol ester comprises plant sterol fatty acid esters and/or plant stanol fatty acid esters that are semi-solid or solid at room temperatures. Preferably plant sterol ester and/or plant stanol ester is in a semi-solid or solid form in the gelled emulsion, of the invention.

Plant stanol fatty acid ester and the cholesterol lowering effects thereof, as well as a suitable method for its preparation, are disclosed in e.g. U.S. Pat. No. 6,174,560. Obviously also plant sterol esters can efficiently be produced by the production method disclosed in U.S. Pat. No. 6,174,560. Alternatively fatty acid esters of plant sterols and/or plant stanols can be produced by any suitable food grade method disclosed in the art. Commercially available plant sterol ester and/or plant stanol ester ingredients e.g. from Raisio Nutrition Ltd or BASF can be used. Commercial ingredients contain small amounts of plant sterols and/or plant stanols in free form (typically less than 3% of the ingredient). In this invention the term "plant sterol ester and/or plant stanol ester" refers only to plant sterols and/or plant stanols in esterified form, and thus the content of "plant sterol ester and/or plant stanol ester" is calculated only by taking into account the plant sterols and/or plant stanols in esterified form contained in the dietary supplement product.

The cholesterol lowering effects of plant sterols and/or plant stanols have been found to be additive both to the cholesterol lowering effect of statins and to the cholesterol lowering effect of healthy diets, such as low-saturated-fat and low-cholesterol diets. Thus the edible product, such as a dietary supplement product of the present invention can be used both as such and in combination with cholesterol lowering drugs and/or cholesterol lowering diets.

According to the invention the amount of plant sterol ester and/or plant stanol ester is at least 20%, preferably at least 25%, more preferably at least 30%, still more preferably at least 35%, even more preferably at least 40%, further more preferably at least 42%, still further more preferably at least 45%, even further more preferably at least 48%, still even further more preferably at least 50% and most preferably at least 52% by weight of the gelled emulsion. The amount of plant sterol ester and/or plant stanol ester is preferably at most 80%, more preferably at most 75%, still more preferably at most 73%, even more preferably at most 70% and most preferably at most 68% by weight of the gelled emulsion. Preferably the plant sterol ester and/or plant stanol ester content of the gelled emulsion may be, and preferably is, 20-80%, more preferably 30-80%, still more preferably 35-75%, even more preferably 40-75%, further more preferably 45-73%, still further more preferably 48-70%, even further more preferably 50-70% and most preferably 52-68% by weight.

By "gelling agent" is meant any edible polymer compound that is capable of forming a gelled emulsion either on its own or together with other compounds (e.g. Ca-ions). Examples of such gelling agents include gel forming proteins, such as gelatin, and gel forming polysaccharides, which may be derived from plants, animals, algae, microbes or may be synthetic. It should be noted that not all proteins and polysaccharides that are used as thickening agents in foods are capable of forming gels. Preferably the gelling agent is a protein, a polysaccharide or mixtures thereof. If the gelling agent is a protein, it is preferably gelatin. Suitable gelling agents are for example gelatin, carrageenan, pectin, alginate, gellan gum, agar, gum Arabic, starch, starch derivatives, inulin, xanthan gum, locust bean gum and glucomannan and/or mixtures thereof. The gelled emulsion of the invention can contain one gelling agent or a mixture of two or more gelling agents. Mixtures of different polysaccharides or mixtures of one or more polysaccharide and gelatin may be used. Suitable gelling agents are therefore gelatin, carrageenan, pectin, alginate, gellan gum, agar, starch, starch derivatives, and such polymer compounds which form gels when used together with other polymer compounds, and mixtures thereof. Such polymer compounds that form gels when used together with other polymer compounds are selected from gum Arabic, inulin, xanthan gum, locust bean gum and glucomannan. Suitable combinations are e.g. a mixture of xanthan gum and locust bean gum, or a mixture of xanthan gum and glucomannan. Other suitable combinations are mixtures of inulin and another gelling agent such as gelatin, gellan gum, carrageenan or pectin. More preferably the gelling agent is selected from gelatin, carrageenan, pectin, alginate, gellan gum, agar or mixtures thereof. Still more preferably the gelling agent contains gelatin. Even more preferably the gelling agent contains gelatin and one or more other gelling agent selected from the group consisting of carrageenan, pectin, alginate, gellan gum and agar. Further more preferably the gelling agent contains gelatin in an amount of at least 50%, more preferably at least 60%, still more preferably at least 70%, even more preferably at least 80% and most preferably at least 90% of the total amount of gelling agent. Most preferably the gelling agent is gelatin.

Gelatin is a protein produced by a partial hydrolysis of collagen, the principal constituent of animal skin, bone and connective tissue. Gelatin is produced by treating the collagen raw material with dilute acid (type A gelatin) or alkali (type B gelatin). Gelatin is most often derived from porcine or bovine origins, but also poultry or fish can be used as a gelatin source. Gelatin is capable of forming thermally reversible gels, which melt in the mouth. A "Bloom value" is often used to characterize the gel strength of a gelatin. Commercial mammalian gelatins usually have a Bloom value between 50 and 300. Fish gelatins may be produced from cold water or warm water fish species. Fish gelatins tend to have lower gelling and melting temperatures as compared to bovine gelatins, but usually relatively higher viscosities than corresponding mammalian gelatins, and are often considered as having sub-optimal functional properties compared to mammalian gelatins. The gels formed with fish gelatin usually tend to be less stable than the gels formed with mammalian gelatin.

In the gelled emulsion of the present invention, the gelling agent preferably comprises gelatin. Gelatin from mammal and/or fish origin may be used. Preferably the gelatin is a low or medium viscosity gelatin. Also gelatin hydrolysates or modified gelatins, such as chemically or enzymatically modified gelatins may be used. Enzyme modified gelatins may be for example gelatins crosslinked by using enzymes, such as transglutaminase, polyphenol oxidase, lipoxygenase, tyrosinase, lysyl oxidase or peroxidase. Also mixtures of different gelatins may be used. A preferred gelatin has a Bloom value of at most 300, preferably at most 280, more preferably at most 260, still more preferably at most 230 and most preferably at most 200. A preferred gelatin has a Bloom value of at least 80, preferably at least 120. Preferably the gelatin has a Bloom value of 80-300, more preferably 120-280, still more preferably 120-260, even more preferably 120-230, and most preferably 120-200. A preferred gelatin has a low or medium viscosity, preferably for example at most 6 mPas, more preferably at most 5 mPas, still more preferably at most 4.5 mPas, even more preferably at most 4.2 mPas, further more preferably at most 3.5 mPas and most preferably at most 3 mPas (when the dynamic viscosity of a 6.67% gelatin water solution is measured at 60° C. by the Official Procedure of the Gelatin Manufacturers Institute of America, Inc., 2013).

The total amount of the gelling agent is at most 15%, preferably at most 14%, more preferably at most 13%, still more preferably at most 12%, even more preferably at most 11% and most preferably at most 10% by weight of the gelled emulsion. The total amount of the gelling agent is preferably at least 0.1%, more preferably at least 0.2%, still more preferably at least 0.3%, even more preferably at least 0.4% and most preferably at least 0.5% by weight of the gelled emulsion. Preferably the total amount of the gelling agent is 0.1-15%, more preferably 0.2-14%, still more preferably 0.3-12%, even more preferably 0.4-11% and most preferably 0.5-10% by weight of the gelled emulsion.

In the embodiments, where the gelling agent is gelatin, the amount of gelatin is typically at least 1.0%, preferably at least 2.0%, more preferably at least 2.5%, still more preferably at least 3.0%, even more preferably at least 3.5% and most preferably at least 4.0% by weight of the gelled emulsion. In the embodiments, where the gelling agent is gelatin, the amount of gelatin is typically at most 15%, preferably at most 14%, more preferably at most 13%, still more preferably at most 12%, even more preferably at most 11% and most preferably at most 10% by weight of gelled emulsion. In the embodiments, where the gelling agent is gelatin, the amount of gelatin is typically 1.0-15%, preferably 2.0-14%, more preferably 2.5-13%, still more preferably 3.0-12%, even more preferably 3.5-11%, and most preferably 4.0-10% by weight of the gelled emulsion. In the embodiments, where the gelling agent comprises polysaccharide(s) or a mixture of gelatin and polysaccharide(s), the total amount of the gelling agent is typically lower than in the embodiments where the gelling agent is gelatin.

It has surprisingly been found that gelled emulsions having a high weight ratio of the active ingredient, i.e. plant sterol ester and/or plant stanol ester, to the gelling agent can be prepared and the organoleptic properties of the gelled emulsions are good. The gelled emulsions of the present invention need to have good texture and mouthfeel. The mouthfeel and texture are not sticky, gummy or hard, but soft and chewable. The mouthfeel is not oily or greasy either, and the gelled emulsion retains the plant sterol ester and/or plant stanol ester in the gelled matrix, despite the high concentration of plant sterol ester and/or plant stanol ester. Therefore, the weight ratio of plant sterol ester and/or plant stanol ester to the total amount of gelling agent is preferably at least 6.0, more preferably at least 6.5, still more preferably at least 7.0, even more preferably at least 7.5, and most preferably at least 8.0. In the embodiments, where the gelling agent is gelatin, the weight ratio of plant sterol ester and/or plant stanol ester to the gelling agent is preferably at most 45, more preferably at most 40, still more preferably at most 35, even more preferably at most 30 and most preferably at most 25 and/or preferably at least 6.0, more preferably at least 6.5, still more preferably at least 7.0, even more preferably at least 7.5, and most preferably at least 8.0.

In a preferred embodiment, the amount of plant sterol ester and/or plant stanol ester in the gelled emulsion is at least 35% by weight and the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0.

In another preferred embodiment, the amount of plant sterol ester and/or plant stanol ester in the gelled emulsion is at least 40% by weight and the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0.

In still another preferred embodiment, the amount of plant sterol ester and/or plant stanol ester in the gelled emulsion is at least 45% by weight and the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0.

In still another preferred embodiment, the amount of plant sterol ester and/or plant stanol ester in the gelled emulsion is at least 52% by weight and the weight ratio of plant sterol ester and/or plant stanol ester to the gelling agent, which preferably is gelatin, is at least 6.5, more preferably at least 7.0, still more preferably at least 7.5, and most preferably at least 8.0.

The total amount of the gelling agent is preferably at most 150%, more preferably at most 120%, still more preferably at most 100%, even more preferably at most 90%, further more preferably at most 80%, and most preferably at most 70% by weight of the amount of water in the gelled emulsion. In the embodiments, where the gelling agent is gelatin, the amount of gelatin is preferably at most 55%, more preferably at most 50%, still more preferably at most 45% and most preferably at most 40% by weight of the amount of water in the gelled emulsion. Preferably in embodiments, where the gelling agent is gelatin, the amount of gelatin is 15-55%, more preferably 20-50%, still more preferably 22-45% and most preferably 25-40% by weight of the amount of water in the gelled emulsion. It is surprising that in a gelled emulsion with a high concentration of plant sterol ester and/or plant stanol ester the amount of gelatin (% by weight) of the amount of water is this low. Gummy and sticky texture and mouthfeel can be avoided, but still the plant sterol ester and/or plant stanol ester is retained in the gelled matrix, and the texture and mouthfeel of the gelled emulsion is not oily either.

Gelling of the emulsion of the present invention is greatly affected by the nature and concentration of different compounds in the emulsion. One of the important determinants is the water content of the emulsion. If the water content is too high or too low, gelling of the emulsion is disturbed and the organoleptic properties of the gelled emulsion weakened. The water content of the gelled emulsion according to the invention is thus at least 3%, preferably at least 8% by weight and at most 35%, preferably at most 28% by weight. Therefore, the water content of the gelled emulsion is 3.0-35%, preferably 4.0-34%, more preferably 5.0-33%, still more preferably 6.0-32%, even more preferably 7.0-31%, further more preferably 8.0-30%, still further more preferably 9.0-29%, even further more preferably 10-28% and most preferably 11-27% by weight. Despite the relatively high water content of the gelled emulsion in some embodiments of this invention, the water activity of the gelled emulsion is low. The water activity, $a_w$, of the gelled emulsion is preferably at most 0.90, more preferably at most 0.87, still more preferably at most 0.85, even more preferably at most 0.80 and most preferably at most 0.75.

Preferably the gelled emulsion of the invention comprises 0-20%, more preferably 0-15%, and still more preferably 0-10.0% by weight triglyceride fat. By "triglyceride fat" is meant edible fats and oils, such as vegetable oils and fish oils. Triglyceride fat can also be a mixture of different edible fats and/or oils. Even more preferably the amount of triglyceride fat is 0-9.0%, further more preferably 0-8.0%, still further more preferably 0-6.0%, even further more preferably 0-4.0%, still even further more preferably 0-2.0% and most preferably 0-0.1% by weight of the gelled emulsion. If there is triglyceride fat present in the gelled emulsion, preferably the weight ratio of the plant sterol ester and/or plant stanol ester to the triglyceride fat is at least 1.0, more preferably at least 1.3, still more preferably at least 1.5, even more preferably at least 1.7, further more preferably at least 2.0, still further more preferably at least 3.0, even further more preferably at least 4.0, still even further more preferably at least 5.0, even still further more preferably at least 6.0 and most preferably at least 13.

Preferably the gelled emulsion of the invention comprises one or more polyols (here also called polyol(s)). By "polyol" is meant compounds that are chemically alcohols with multiple hydroxyl groups, and can be used in foods and/or dietary supplements. Examples of the polyols include sugar alcohols, propylene glycol and glycerol. Typical sugar alcohols are for example sorbitol, xylitol, erythritol, mannitol, maltitol, isomalt and lactitol. Preferably the gelled emulsion comprises glycerol, sorbitol, xylitol, erythritol or a mixture of at least two of these, more preferably glycerol, sorbitol, xylitol or a mixture of at least two of these, and most preferably glycerol and/or xylitol. The polyol is preferably glycerol, sorbitol, xylitol, erythritol or a mixture of at least two of these, more preferably glycerol, sorbitol, xylitol or a mixture of at least two of these, most preferably glycerol and/or xylitol. A preferred mixture of polyols is a mixture of glycerol and xylitol, where the amount of glycerol is preferably at least 5% of the total amount of glycerol and xylitol. Preferably in this mixture the weight ratio of glycerol to xylitol is 0.05-10 (i.e. the amount of glycerol is from 5% to 1000% of the amount of xylitol in the gelled emulsion). More preferably the weight ratio of glycerol to xylitol is 0.08-2.0, still more preferably 0.11-1.0, even more preferably 0.14-0.8, and most preferably 0.16-0.5. Another preferred mixture of polyols is a mixture of xylitol and sorbitol, where the weight ratio of xylitol to sorbitol is 1.0-3.0 (i.e. the amount of xylitol is from 100% to 300% of the amount of sorbitol in the gelled emulsion). More preferably the weight ratio of xylitol to sorbitol is 1.2-2.8, still more preferably 1.5-2.5, and most preferably 1.7-2.2.

It has surprisingly been noticed that polyols further improve the organoleptic properties, especially texture, of the gelled emulsion of the present invention. Furthermore, polyols also bring improvement into the processing of the emulsion before gelling. The gelled emulsion of the invention contains one or more polyols in an amount of 0-60% by weight. The total amount of polyols may be at least 1.0%, preferably at least 2.0%, more preferably at least 3.0%, still more preferably at least 4.0% and most preferably at least 5.0% by weight of the gelled emulsion and at most 60%, preferably at most 50%, more preferably at most 40%, still more preferably at most 35%, even more preferably at most 30% and most preferably at most 25% by weight of the gelled emulsion. Preferably the total amount of polyols is 1.0-60%, more preferably 1.0-50%, still more preferably 2.0-50%, even more preferably 3.0-40%, further more preferably 4.0-35%, still further more preferably 4.0-30%, even further more preferably 5.0-30%, still even further more preferably 5.0-25% and most preferably 5.0-20% by weight of the gelled emulsion.

If glycerol is used, preferably the amount of glycerol is at least 5%, more preferably at least 10%, still more preferably at least 15%, even more preferably at least 20%, further more preferably at least 50%, still further more preferably at least 70% and most preferably at least 85% by weight of the total amount of polyols in the gelled emulsion. Preferably the amount of glycerol is at least 1%, more preferably at least 3%, still more preferably at least 5%, even more preferably at least 6%, further more preferably at least 7%, still further more preferably at least 8% and most preferably at least 9% by weight of the gelled emulsion. Preferably the amount of glycerol is 1-30%, more preferably 3-30%, still more preferably 5-30%, even more preferably 6-28%, further more preferably 7-25%, still further more preferably 8-22% and most preferably 9-20% by weight of the gelled emulsion.

Glycerol is preferably used as a mixture of glycerol and at least one other polyol, for example xylitol, sorbitol or erythritol. A preferred mixture is a mixture of glycerol and xylitol, where the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5.

Another preferred mixture is a mixture of glycerol, xylitol and sorbitol, where the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2.

If xylitol is used, preferably the amount of xylitol is at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the amount of xylitol is at least 1%, more preferably at least 2%, still more preferably at least 3%, even more preferably at least 4%, and most preferably at least 5% by weight of the gelled emulsion. Preferably the amount of xylitol is 1-30%, more preferably 2-28%, still more preferably 3-25%, even more preferably 4-23%, most preferably 5-20% by weight of the gelled emulsion.

Xylitol is preferably used as a mixture of xylitol and at least one other polyol, for example glycerol, sorbitol or erythritol. A preferred mixture is a mixture of xylitol and sorbitol, in which the weight ratio of xylitol to sorbitol is 1.0-3.0, more preferably 1.2-2.8, still more preferably 1.5-2.5, and most preferably 1.7-2.2. Another preferred mixture is a mixture of xylitol, erythritol and sorbitol, where the amount of xylitol is preferably at least 5%, more preferably at least 10%, still more preferably at least 15%, even more preferably at least 20%, and most preferably at least 40% by weight of the total amount of xylitol, sorbitol and erythritol.

Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. It has surprisingly been found that gelled emulsions having a high weight ratio of the active ingredient, i.e. plant sterol ester and/or plant stanol ester, to the total amount of polyols can be prepared and still the organoleptic properties of the gelled emulsions are good.

In a preferred embodiment, the amount of plant sterol ester and/or plant stanol ester in the gelled emulsion is at least 35% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain glycerol in an amount of at least 5%, more preferably at least 10%, still more preferably at least 15%, even more preferably at least 20%, further more preferably at least 50%, still further more preferably at least 70% and most preferably at least 85% by weight of the total amount of polyols in the gelled emulsion. In this embodiment, it is further preferred that the polyols contain, and more preferably is a mixture of glycerol and xylitol, or a mixture of glycerol, xylitol and sorbitol. When the polyols contain, and preferably is a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain, and preferably is a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2.

In another preferred embodiment, the amount of plant sterol ester and/or plant stanol ester in the gelled emulsion is at least 35% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. In this embodiment, it is further preferred that the polyols comprise, and more preferably is a mixture of xylitol and sorbitol, where the weight ratio of xylitol to sorbitol is 1.0-3.0, preferably 1.2-2.8, more preferably 1.5-2.5, and most preferably 1.7-2.2.

In still another preferred embodiment, the amount of plant sterol ester and/or plant stanol ester in the gelled emulsion is at least 40% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain glycerol in an amount of at least 5%, more preferably at least 10%, still more preferably at least 15%, even more preferably at least 20%, further more preferably at least 50%, still further more preferably at least 70% and most preferably at least 85% by weight of the total amount of polyols in the gelled emulsion. In this embodiment, it is further preferred that the polyols contain, and more preferably is a mixture of glycerol and xylitol, or a mixture of glycerol, xylitol and sorbitol. When the polyols contain, and preferably is a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture the weight ratio of glycerol to xylitol is 0.05-10, more preferably 0.08-2.0, still more preferably 0.11-1.0, even more preferably 0.14-0.8, and most preferably 0.16-0.5. When the polyols contain, and preferably is a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2.

In still another preferred embodiment, the amount of plant sterol ester and/or plant stanol ester in the gelled emulsion is at least 40% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. In this embodiment, it is further preferred that the polyols comprise, and more preferably is a mixture of xylitol and sorbitol, where the weight ratio of xylitol to sorbitol is 1.0-3.0, preferably 1.2-2.8, more preferably 1.5-2.5, and most preferably 1.7-2.2.

In still another preferred embodiment, the amount of plant sterol ester and/or plant stanol ester in the gelled emulsion is at least 45% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain glycerol in an amount of at least 5%, more preferably at least 10%, still more preferably at least 15%, even more preferably at least 20%, further more preferably at least 50%, still further more preferably at least 70% and most preferably at least 85% by weight of the total amount of polyols in the gelled emulsion. In this embodiment, it is further preferred that the polyols contain, and more preferably is a mixture of glycerol and xylitol, or a mixture of glycerol, xylitol and sorbitol. When the polyols contain, and preferably is a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain, and preferably is a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2.

In still another preferred embodiment, the amount of plant sterol ester and/or plant stanol ester in the gelled emulsion is at least 45% by weight and the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. In this embodiment, preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. In this embodiment, it is further preferred that the polyols comprise, and more preferably is a mixture of xylitol and sorbitol, where the weight ratio of xylitol to sorbitol is 1.0-3.0, preferably 1.2-2.8, more preferably 1.5-2.5, and most preferably 1.7-2.2.

The gelled emulsion of the invention may also contain other ingredients, for example sweeteners, flavors, pH modifiers, colors, emulsifiers, stabilizers, antioxidants and preservatives. The gelled emulsion may also contain other ingredients with beneficial health effects, for example vitamins (e.g. C, D, E and K vitamins), minerals, antioxidants and/or polyphenols.

The taste of the plant sterol ester and/or plant stanol ester is bland, and does not require any masking. However, if desired, the gelled emulsion of the invention may be flavored or sweetened. For example fruit or berry flavors may be utilized, for example citrus flavors. Natural or artificial sweeteners may be used. Sugar based natural sweeteners include for example sucrose, sugar syrups, fructose, glucose, maltose and dextrins. Artificial sweeteners include, but are not limited to, e.g. aspartame, stevia, sucralose, acesulfame-K, saccharin and cyclamates. Cariogenic sugars selected from the group consisting of sucrose, glucose fructose, maltose and lactose may also be included in the gelled emulsion. Preferably the total amount of cariogenic sugars is low, preferably at most 20%, more preferably at most 15%, still more preferably at most 10%, even more preferably at most 5% and further more preferably 0-0.1% by weight of the gelled emulsion. Most preferably there are no cariogenic sugars present in the gelled emulsion. By "cariogenic sugars" is here meant sugars producing or promoting the development of dental caries selected from the group consisting of sucrose, glucose fructose, maltose and lactose. Limiting the amount of cariogenic sugars is not only a health issue, but surprisingly it also brought on a further improvement into processing of the emulsion.

Food grade acids and/or buffering agents may be used as pH modifiers. Suitable acids include for example citric acid, malic acid, lactic acid, fumaric acid, tartaric acid, acetic acid and phosphoric acid. Suitable buffering agents include for example the salts of the before mentioned acids. Preferred acids include citric acid and malic acid, and preferred buffering agents include their salts. Preferably the total amount of the acids and/or buffering agents is less than 15%, more preferably less than 13%, still more preferably less than 10%, even more preferably less than 8.0% and most preferably less than 6.0% by weight of the gelled emulsion. In another preferred embodiment the gelled emulsion does not contain a buffering agent, but the desired pH is achieved otherwise, e.g. by using only an acid. If no acidic taste or pH is desired, the gelled emulsion may be prepared without the use of an acid.

The gelled emulsion of the present invention can preferably be prepared according to the following method, which is a further object of the present invention. The method comprises at least the following steps:

a) preparing an aqueous phase by mixing water and gelling agent, and optionally other water soluble ingredients, preferably at a temperature of at least 40° C., b) melting plant sterol ester and/or plant stanol ester, preferably at a temperature of at least 40° C., more preferably at 40-80° C., and optionally mixing it with other lipid soluble ingredients, c) emulsifying the melted plant sterol ester and/or plant stanol ester, or the mixture of plant sterol ester and/or plant stanol ester and other lipid soluble ingredients, with the aqueous phase, preferably at a temperature of at least 40° C., more preferably at 40-80° C., still more preferably at 45-70° C. and most preferably at 45-60° C.

d) feeding the obtained emulsion, preferably at a temperature of at least 40° C., into moulds, preferably into dose unit moulds, and e) allowing the emulsion to cool to or below the gelation temperature of the aqueous phase, and thus preferably to solidify, to obtain the gelled emulsion.

The edible product, such as a dietary supplement product of the present invention can preferably be prepared according to the following method. The method comprises at least the following steps:

a) preparing an aqueous phase by mixing water and gelling agent, and optionally other water soluble ingredients, preferably at a temperature of at least 40° C., b) melting plant sterol ester and/or plant stanol ester, preferably at a temperature of at least 40° C., more preferably at 40-80° C., and optionally mixing it with other lipid soluble ingredients, c) emulsifying the melted plant sterol ester and/or plant stanol ester, or the mixture of plant sterol ester and/or plant stanol ester and other lipid soluble ingredients, with the aqueous phase, preferably at a temperature of at least 40° C., more preferably at 40-80° C., still more preferably at 45-70° C. and most preferably at 45-60° C.

d) feeding the obtained emulsion, preferably at a temperature of at least 40° C., into dose unit moulds, e) allowing the emulsion to cool to or below the gelation temperature of the aqueous phase to obtain a dose unit of the gelled emulsion, f) optionally coating the dose unit, and g) packing the obtained dose unit.

Preferably the method includes no coating step f. It is also preferred that the dose unit is packed in a blister.

Despite the high plant sterol ester and/or plant stanol ester content, the viscosity of the emulsion before the gelling is within the range allowing further processing, e.g. dosing into moulds, preferably into the dose unit moulds. The type of production line, e.g. dosing nozzles and packaging line sets requirements on the viscosity range. The recipe can be modified to fulfil the viscosity requirements set by the individual production lines. Also the shear rate that is used at the emulsification step affects the viscosity of the emulsion formed. E.g. the viscosity of the emulsion can be reduced by reducing the share rate.

The viscosity of the emulsion before the gelling can be preferably at most 40 000 mPas, more preferably at most 30 000 mPas and most preferably at most 20 000 mPas (measured with Brookfield viscometer, 1.5 rpm, at 55° C., 5 minutes). Preferably the viscosity is at least 5000 mPas.

It has surprisingly been found that the gelled emulsion having a high plant sterol ester and/or plant stanol ester content can be prepared according to the present invention without having unacceptably high viscosity of the emulsion before the gelling, and still retaining a good emulsion stability. Still the gelling property of the emulsion is good and the final gelled product has the desired organoleptic properties with no fatty mouthfeel.

The dose units of the gelled emulsion may be produced by feeding the emulsion into stationary or moving moulds. The feeding takes place preferably via nozzles or needles using appropriate pressure. The moulds are preferably dose unit moulds, such as hollow blisters or cavities produced from at least one film, e.g. plastic-coated aluminum foil. These blisters or cavities are sealed after filling e.g. with a releasable cover film or foil. However, the gelled emulsion may also be removed from the moulds followed by separate end-use packaging. If gelling was not performed in dose unit moulds but in bigger moulds, the gelled emulsion may be removed from the used moulds and cut into dose units before the end-use packaging. The removed gelled dose units may also be coated by any suitable coating procedure and coating material e.g. chewable soft gel coatings or sugar alcohols such as sorbitol or maltitol. The edible product, e.g. a dietary supplement product of the invention is preferably packaged in a blister or a blister pack, preferably in an aluminium blister for excellent water retaining and barrier properties. Canadian patent number 1289074 describes ways to produce usable uncoated administration forms packed e.g. in blisters. The aqueous phase has preferably a gelling temperature from 10° C. to 35° C., more preferably from 12° C. to 33° C. and most preferably from 15° C. to 30° C. The pH of the aqueous phase is preferably from 2 to 9, more preferably from 2.5 to 8 and most preferably from 3 to 7.

All operations during the processing are preferably done at inert atmosphere. Optionally the emulsion is degassed before dosing into dose units. Despite the high plant sterol ester and/or plant stanol ester content, the emulsion stability during the processing before gelling is good. If desired, the gelled emulsion may be more than biphasic, i.e. a double emulsion. Preferably the gelled emulsion is an oil-in-water (O/W) emulsion.

The dose units of the gelled emulsion may optionally be dried before packaging, but in preferred embodiments drying is not used. If the water content of the dose units of the gelled emulsion is undesired high, the dose units are dried after step e) to obtain the desired level. The dose units may be coated, but preferably they are uncoated. Preferably the dose units are individually packaged. However if the dose units are coated also several dose units may be packed in one package. The size of the dose unit of the gelled emulsion is preferably at least 0.3 g, more preferably at least 0.7 g and most preferably at least 1.0 g. The size of the dose unit of the gelled emulsion is preferably at most 12.5 g, more preferably at most 7 g, and most preferably at most 6 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g.

Because the gelled emulsion of the invention has a high plant sterol ester and/or plant stanol ester content, the daily dose of plant sterol ester and/or plant stanol ester can be incorporated in a small amount of the gelled emulsion. The preferred daily dose of plant sterol ester and/or plant stanol ester is at least 0.8 g, more preferably at least 1.3 g, still more preferably at least 1.7 g, even more preferably at least 2.5 g and most preferably the daily dose of plant sterol ester and/or plant stanol ester is at least 3.4 g. The preferred daily dose of plant sterol ester and/or plant stanol ester is at most 15 g, more preferably at most 13 g, still more preferably at most 12 g, even more preferably at most 11 g and most preferably at most 10 g.

The daily dose of plant sterol ester and/or plant stanol ester is preferably provided by 1.0-25 g of the gelled emulsion. Thus the daily dose of the gelled emulsion is preferably 1.0-25 g. More preferably the daily dose of the gelled emulsion is 1.3-20 g, still more preferably 1.5-17 g, even more preferably 1.8-15 g, and most preferably 2.0-13 g. The daily dose of the gelled emulsion can be provided in one or more servings. Preferably the daily dose of the gelled emulsion is provided by one to four servings, more preferably in one or two servings, and most preferably in one serving. By a "serving" is meant the recommended amount of dose units of the gelled emulsion to be consumed at the same intake occasion. The size of the dose unit is dependent on the size of the mould wherein the emulsion is gelled.

The energy content of the gelled emulsion is preferably at most 840 kJ, more preferably at most 670 kJ, still more preferably at most 500 kJ, even more preferably at most 330 kJ and most preferably at most 200 kJ per daily dose of the gelled emulsion. The energy content of the gelled emulsion is preferably at least 4 kJ, more preferably at least 8 kJ, still more preferably at least 12 kJ, even more preferably at least 16 kJ and most preferably at least 20 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ.

Embodiment 1a

A preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 25-80% by weight, gelling agent in an amount of at most 13% by weight, and water in an amount of 5.0-33% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The plant sterol ester and/or plant stanol ester preferably contains plant stanol ester in an amount of at least 10%, more preferably at least 50%, still more preferably at least 70% and most preferably at least 90% by weight. The gelling agent preferably contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. The water activity, $a_w$, of the gelled emulsion is at most 0.80 and preferably at most 0.75. Further, the gelled emulsion preferably contains 0-20%, more preferably 0-15%, still more preferably 0-10.0%, even more preferably 0-9.0%, further more preferably 0-8.0%, still further more preferably 0-6.0%, even further more preferably 0-4.0%, still even further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 1.3, more preferably at least 1.7, still more preferably at least 2.0, even more preferably at least 3.0, further more preferably at least 4.0, still further more preferably at least 5.0, even further more preferably at least 6.0 and most preferably at least 13. The gelled emulsion preferably contains one or more polyols in an amount of 1.0-50%, more preferably 2.0-50%, still more preferably 3.0-40%, even more preferably 4.0-35%, further more preferably 5.0-30%, still further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 1b

Another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 25-80% by weight, gelling agent in an amount of at most 13% by weight, and water in an amount of 5.0-33% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The plant sterol ester and/or plant stanol ester preferably contains plant stanol ester in an amount of at least 10%, more preferably at least 50%, still more preferably at least 70% and most preferably at least 90% by weight. The gelling agent preferably contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. The water activity, $a_w$, of the gelled emulsion is at most 0.80 and preferably at most 0.75. Further, the gelled emulsion preferably contains 0-20%, more preferably 0-15%, still more preferably 0-10.0%, even more preferably 0-9.0%, further more preferably 0-8.0%, still further more preferably 0-6.0%, even further more preferably 0-4.0%, still even further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 1.3, more preferably at least 1.7, still more preferably at least 2.0, even more preferably at least 3.0, further more preferably at least 4.0, still further more preferably at least 5.0, even further more preferably at least 6.0 and most preferably at least 13. The gelled emulsion preferably contains one or more polyols in an amount of 1.0-50%, more preferably 2.0-50%, still more preferably 3.0-40%, even more preferably 4.0-35%, further more preferably 5.0-30%, still further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 2a

A preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 35-75% by weight, gelling agent in an amount of at most 12% by weight, and water in an amount of 5.0-33% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The plant sterol ester and/or plant stanol ester preferably contains plant stanol ester in an amount of at least 10%, more preferably at least 50%, still more preferably at least 70% and most preferably at least 90% by weight. The gelling agent preferably contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. The water activity, $a_w$, of the gelled emulsion is at most 0.80 and preferably at most 0.75. Further, the gelled emulsion preferably contains 0-20%, more preferably 0-15%, still more preferably 0-10.0%, even more preferably 0-9.0%, further more preferably 0-8.0%, still further more preferably 0-6.0%, even further more preferably 0-4.0%, still even further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 1.7, more preferably at least 2.0, still more preferably at least 3.0, even more preferably at least 4.0, further more preferably at least 5.0, still further more preferably at least 6.0 and most preferably at least 13. The gelled emulsion preferably contains one or more polyols in an amount of 1.0-50%, more preferably 2.0-50%, still more preferably 3.0-40%, even more preferably 4.0-35%, further more preferably 5.0-30%, still further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 2b

Another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 35-75% by weight, gelling agent in an amount of at most 12% by weight, and water in an amount of 5.0-33% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The plant sterol ester and/or plant stanol ester preferably contains plant stanol ester in an amount of at least 10%, more preferably at least 50%, still more preferably at least 70% and most preferably at least 90% by weight. The gelling agent preferably contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. The water activity, $a_w$, of the gelled emulsion is at most 0.80 and preferably at most 0.75. Further, the gelled emulsion preferably contains 0-20%, more preferably 0-15%, still more preferably 0-10.0%, even more preferably 0-9.0%, further more preferably 0-8.0%, still further more preferably 0-6.0%, even further more preferably 0-4.0%, still even further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 1.7, more preferably at least 2.0, still more preferably at least 3.0, even more preferably at least 4.0, further more preferably at least 5.0, still further more preferably at least 6.0 and most preferably at least 13. The gelled emulsion preferably contains one or more polyols in an amount of 1.0-50%, more preferably 2.0-50%, still more preferably 3.0-40%, even more preferably 4.0-35%, further more preferably 5.0-30%, still further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 Id and most preferably at most 20 kJ. Preferably the gelled emulsion of this embodiment is uncoated.

Embodiment 3a

Another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 40-75% by weight, gelling agent in an amount of at most 12% by weight, and water in an amount of 6.0-32% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent preferably contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. Further in this embodiment, the water activity, $a_w$, of the gelled emulsion is at most 0.80 and preferably at most 0.75. Further, the gelled emulsion contains 0-10.0%, preferably 0-9.0%, more preferably 0-8.0%, still more preferably 0-6.0%, even more preferably 0-4.0%, further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 4.0, more preferably at least 5.0, still more preferably at least 6.0 and most preferably at least 13. The gelled emulsion preferably contains one or more polyols in an amount of 1.0-40%, more preferably 2.0-40%, still more preferably 3.0-40%, even more preferably 4.0-35%, further more preferably 5.0-30%, still further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 3b

Another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 40-75% by weight, gelling agent in an amount of at most 12% by weight, and water in an amount of 6.0-32% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent preferably contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. Further in this embodiment, the water activity, $a_w$, of the gelled emulsion is at most 0.80 and preferably at most 0.75. Further, the gelled emulsion contains 0-10.0%, preferably 0-9.0%, more preferably 0-8.0%, still more preferably 0-6.0%, even more preferably 0-4.0%, further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 4.0, more preferably at least 5.0, still more preferably at least 6.0 and most preferably at least 13. The gelled emulsion preferably contains one or more polyols in an amount of 1.0-40%, more preferably 2.0-40%, still more preferably 3.0-40%, even more preferably 4.0-35%, further more preferably 5.0-30%, still further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 id. Preferably the gelled emulsion of this embodiment is uncoated.

Embodiment 3c

Another preferred embodiment of the present invention is a dietary supplement product, more preferably a serum LDL cholesterol lowering dietary supplement product, which comprises a gelled emulsion containing plant sterol ester and/or plant stanol ester in an amount of 40-75% by weight, gelatin in an amount of 3.0-12% by weight, and water in an amount of 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. The amount of gelatin is 22-45% and preferably 25-40% by weight of the amount of water in the gelled emulsion. The weight ratio of plant sterol ester and/or plant stanol ester to gelatin is at least 6.0, preferably at least 6.5, more preferably at least 7.0, still more preferably at least 7.5, and most preferably at least 8.0. Further in this embodiment, the water activity, $a_w$, of the gelled emulsion is at most 0.80 and preferably at most 0.75. Further, the gelled emulsion contains 0-2.0% and preferably 0-0.1% by weight triglyceride fat. The gelled emulsion contains one or more polyols in an amount of 5.0-25% and preferably 5.0-20% by weight. It is preferred that the polyols contain a mixture of glycerol and xylitol. When the polyols contain a mixture of glycerol and xylitol, the amount of glycerol is preferably at least 10%, more preferably at least 12%, and most preferably at least 14% by weight of the total amount of glycerol and xylitol. The weight ratio of plant sterol ester and/or plant stanol ester to the total amount of polyols is preferably at least 1.7, more preferably at least 2.0, still more preferably at least 2.5, and most preferably at least 3.0. Preferably the total amount of cariogenic sugars is 0-0.1% by weight of the gelled emulsion. Most preferably there are no cariogenic sugars present in the gelled emulsion. Preferably the total amount of the acids and/or buffering agents is less than 6.0% by weight of the gelled emulsion. The daily dose of the gelled emulsion of this embodiment is preferably 2.0-13 g. The size of the dose unit of the gelled emulsion is preferably 1.0-6.0 g. Preferably the energy content of the gelled emulsion is at most 200 kJ per daily dose of the gelled emulsion. The energy content per gram of the gelled emulsion is preferably at most 20 kJ. Preferably the gelled emulsion of this embodiment is uncoated.

Embodiment 4a

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of at least 42%, preferably at least 45%, more preferably at least 48%, still more preferably at least 50% and most preferably at least 52% by weight of the gelled emulsion, gelling agent in an amount of at most 13% by weight, and water in an amount of 6.0-32% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The amount of plant sterol ester and/or plant stanol ester is in this embodiment preferably at most 80%, more preferably at most 75%, still more preferably at most 73%, even more preferably at most 70% and most preferably at most 68% by weight of the gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent preferably contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. Further in this embodiment, the water activity, $a_w$, of the gelled emulsion is at most 0.80 and preferably at most 0.75. Further, the gelled emulsion contains 0-10.0%, preferably 0-9.0%, more preferably 0-8.0%, still more preferably 0-6.0%, even more preferably 0-4.0%, further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 5.0, more preferably at least 6.0 and most preferably at least 13. Further in this embodiment, the gelled emulsion preferably contains one or more polyols in an amount of 1.0-40%, more preferably 3.0-40%, still more preferably 4.0-35% even more preferably 5.0-30%, further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 4b

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of at least 42%, preferably at least 45%, more preferably at least 48%, still more preferably at least 50% and most preferably at least 52% by weight of the gelled emulsion, gelling agent in an amount of at most 13% by weight, and water in an amount of 6.0-32% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The amount of plant sterol ester and/or plant stanol ester is in this embodiment preferably at most 80%, more preferably at most 75%, still more preferably at most 73%, even more preferably at most 70% and most preferably at most 68% by weight of the gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent preferably contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. Preferably the weight ratio of plant sterol ester and/or plant stanol ester to the gelling agent, which preferably is gelatin, is at least 6.0, more preferably at least 6.5, still more preferably at least 7.0, even more preferably at least 7.5, and most preferably at least 8.0. Further in this embodiment, the water activity, $a_w$, of the gelled emulsion is at most 0.80 and preferably at most 0.75. Further, the gelled emulsion contains 0-10.0%, preferably 0-9.0%, more preferably 0-8.0%, still more preferably 0-6.0%, even more preferably 0-4.0%, further more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 5.0, more preferably at least 6.0 and most preferably at least 13. Further in this embodiment, the gelled emulsion preferably contains one or more polyols in an amount of 1.0-40%, more preferably 3.0-40%, still more preferably 4.0-35% and even more preferably 5.0-30%, further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 5a

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 45-73% by weight, gelling agent in an amount of at most 12% by weight, and water in an amount of 7.0-31% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The gelatin concentration is preferably at least 3.0%, more preferably at least 3.5% and most preferably at least 4.0% by weight of the gelled emulsion. The weight ratio of plant sterol ester and/or plant stanol ester to the gelling agent, which preferably is gelatin, is at least 6.0, preferably at least 6.5, more preferably at least 7.0, still more preferably at least 7.5, and most preferably at least 8.0. Further in this embodiment, the water activity, $a_w$, of the gelled emulsion is at most 0.80 and preferably at most 0.75. Further, the gelled emulsion contains 0-9.0%, preferably 0-8.0%, more preferably 0-6.0%, still more preferably 0-4.0%, even more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 5.0, more preferably at least 6.0 and most preferably at least 13. Further in this embodiment, the gelled emulsion preferably contains one or more polyols in an amount of 1.0-40%, more preferably 3.0-40%, still more preferably 4.0-35% and even more preferably 5.0-30%, further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-

2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 5b

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 45-73% by weight, gelling agent in an amount of at most 12% by weight, and water in an amount of 7.0-31% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 3.0-12%, more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The gelatin concentration is preferably at least 3.0%, more preferably at least 3.5% and most preferably at least 4.0% by weight of the gelled emulsion. The weight ratio of plant sterol ester and/or plant stanol ester to the gelling agent, which preferably is gelatin, is at least 6.0, preferably at least 6.5, more preferably at least 7.0, still more preferably at least 7.5, and most preferably at least 8.0. Further in this embodiment, the water activity, $a_w$, of the gelled emulsion is at most 0.80 and preferably at most 0.75. Further, the gelled emulsion contains 0-9.0%, preferably 0-8.0%, more preferably 0-6.0%, still more preferably 0-4.0%, even more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 5.0, more preferably at least 6.0 and most preferably at least 13. Further in this embodiment, the gelled emulsion preferably contains one or more polyols in an amount of 1.0-40%, more preferably 3.0-40%, still more preferably 4.0-35% and even more preferably 5.0-30%, further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8.0% and most preferably less than 6.0% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 6a

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of at least 48%, preferably at least 50%, and more preferably at least 52% by weight of the gelled emulsion, gelling agent in an amount of at most 13% by weight, and water in an amount of 7.0-31% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The amount of plant sterol ester and/or plant stanol ester is in this embodiment preferably at most 80%, more preferably at most 75%, still more preferably at most 73%, even more preferably at most 70% and most preferably at most 68% by weight of the gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The gelatin concentration is preferably at least 3.0%, more preferably at least 3.5% and most preferably at least 4.0% by weight of the gelled emulsion. The weight ratio of plant sterol ester and/or plant stanol ester to the gelling agent, which preferably is gelatin, is at least 6.0, preferably at least 6.5, more preferably at least 7.0, still more preferably at least 7.5, and most preferably at least 8.0. Further in this embodiment, the water activity, $a_w$, of the gelled emulsion is most 0.80 and preferably at most 0.75. Further, the gelled emulsion contains 0-8.0%, preferably 0-6.0%, more preferably 0-4.0%, still more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 6.0, most preferably at least 13. Further in this embodiment, the gelled emulsion preferably contains one or more polyols in an amount of 1.0-35%, more preferably 3.0-35%, still more preferably 4.0-35% and even more preferably 5.0-30%, further more preferably 5.0-25% and most preferably 5.0-20% by weight. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 6b

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of at least 48%, preferably at least 50%, and more preferably at least 52% by weight of the gelled emulsion, gelling agent in an amount of at most 13% by weight, and water in an amount of 7.0-31% by weight. Preferably the gelled emulsion contains water in an amount of 8.0-30%, more preferably 9.0-29%, still more preferably 10-28% and most preferably 11-27% by weight. Preferably the gelled emulsion is an oil-in-water (O/W) emulsion. Preferably the gelled emulsion is a solid gelled emulsion. The amount of plant sterol ester and/or plant stanol ester is in this embodiment preferably at most 80%, more preferably at most 75%, still more preferably at most 73%, even more preferably at most 70% and most preferably at most 68% by weight of the gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 2.5-13%, more preferably 3.0-12%, still more preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The gelatin concentration is preferably at least 3.0%, more preferably at least 3.5% and most preferably at least 4.0% by weight of the gelled emulsion. The weight ratio of plant sterol ester and/or plant stanol ester to the gelling agent, which preferably is gelatin, is at least 6.0, preferably at least 6.5, more preferably at least 7.0, still more preferably at least 7.5, and most preferably at least 8.0. Further in this embodiment, the water activity, $a_w$, of the gelled emulsion is most 0.80 and preferably at most 0.75. Further, the gelled emulsion contains 0-8.0%, preferably 0-6.0%, more preferably 0-4.0%, still more preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 6.0 and most preferably at least 13. Further in this embodiment, the gelled emulsion preferably contains one or more polyols in an amount of 1.0-35%, more preferably 3.0-35%, still more preferably 4.0-35% and even more preferably 5.0-30%, further more preferably 5.0-25% and most preferably 5.0-20% by weight. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 7a

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 52-68% by weight, gelling agent in an amount of at most 11% by weight, and water in an amount of 8.0-30% by weight. Preferably the gelled emulsion contains water in an amount of 9.0-29%, more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The weight ratio of plant sterol ester and/or plant stanol ester to the gelling agent, which preferably is gelatin, is at least 6.5, preferably at least 7.0, more preferably at least 7.5, and most preferably at least 8.0. Further in this embodiment, the water activity, $a_w$, of the gelled emulsion is at most 0.80 and preferably at most 0.75. Further, the gelled emulsion contains 0-4.0%, preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 13.0. Further in this embodiment, the gelled emulsion contains one or more polyols in an amount 1.0-30%, preferably 4.0-30%, more preferably 5.0-30%, still more preferably 5.0-25% and most preferably 5.0-20% by weight of the dietary supplement product. Preferably the polyols contain glycerol in an amount of at least 5%, more preferably at least 10%, still more preferably at least 15%, even more preferably at least 20%, further more preferably at least 50%, still further more preferably at least 70%, and most preferably at least 85% by weight of the total amount of polyols. In this embodiment, it is further preferred that the polyols contain a mixture of glycerol and xylitol, or a mixture of glycerol, xylitol and sorbitol. When the polyols contain a mixture of glycerol and xylitol, the amount of glycerol is preferably at least 5%, more preferably at least 7%, still more preferably at least 10%, even more preferably at least 12%, and most preferably at least 14% by weight of the total amount of glycerol and xylitol. Preferably in this mixture, the weight ratio of glycerol to xylitol is 0.05-10, more preferably 0.08-2.0, still more preferably 0.11-1.0, even more preferably 0.14-0.8, and most preferably 0.16-0.5. When the polyols contain a mixture of glycerol, xylitol and sorbitol, the amount of glycerol is preferably at least 5%, more preferably at least 7%, still more preferably at least 10%, even more preferably at least 12%, and most preferably at least 14% by weight of the total amount of glycerol, xylitol and sorbitol. Preferably in this mixture, the weight ratio of glycerol to the total amount of xylitol and sorbitol is 0.05-10, more preferably 0.08-2.0, still more preferably 0.11-1.0, even more preferably 0.14-0.8, and most preferably 0.16-0.5. Further in this mixture, the weight ratio of xylitol to sorbitol is preferably 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

Embodiment 7b

Still another preferred embodiment of the present invention is an edible product, preferably a dietary supplement product, more preferably a serum LDL cholesterol lowering dietary supplement product, which comprises a gelled emulsion containing plant sterol ester and/or plant stanol ester in an amount of 52-68% by weight, gelling agent in an amount of at most 11% by weight, and water in an amount of 8.0-30% by weight. Preferably the gelled emulsion contains water in an amount of 9.0-29%, still more preferably 10-28% and most preferably 11-27% by weight. Preferably the gelled emulsion is an oil-in-water (O/W) emulsion. Preferably the gelled emulsion is a solid gelled emulsion. In this embodiment, plant sterol ester and/or plant stanol ester preferably contains plant stanol ester in an amount of at least 10%, more preferably at least 50%, still more preferably at least 70% and most preferably at least 90% by weight of the plant sterol ester and/or plant stanol ester. Further in this embodiment, the gelling agent contains gelatin, preferably in an amount of at least 50% of the total amount of gelling agent. Most preferably the gelling agent is gelatin. When the gelling agent is gelatin, the amount of gelatin is preferably 3.5-11% and most preferably 4.0-10% by weight of the gelled emulsion. Further, when the gelling agent is gelatin, the amount of gelatin is preferably 15-55%, more preferably 20-50%, still more preferably 22-45% and most preferably 25-40% by weight of the amount of water in the gelled emulsion. The weight ratio of plant sterol ester and/or plant stanol ester to the gelling agent, which preferably is gelatin, is p at least 6.5, preferably at least 7.0, more preferably at least 7.5, and most preferably at least 8.0. Further in this embodiment, the water activity, $a_w$, of the gelled emulsion is at most 0.80 and preferably at most 0.75. Further, the gelled emulsion contains 0-4.0%, preferably 0-2.0% and most preferably 0-0.1% by weight triglyceride fat. If triglyceride fat is present in the gelled emulsion, the weight ratio of the plant sterol ester and/or plant stanol ester to the triglyceride fat is preferably at least 13.0. Further in this embodiment, the gelled emulsion contains one or more polyols in an amount 1.0-30%, preferably 4-30%, more preferably 5.0-30%, still more preferably 5.0-25% and most preferably 5.0-20% by weight of the dietary supplement product. Preferably the polyols contain xylitol in an amount of at least 5%, more preferably at least 10%, still more preferably at least 15%, even more preferably at least 20%, further more preferably at least 40%, still further more preferably at least 50%, even further more preferably at least 60%, still even further more preferably at least 65% and most preferably at least 80% by weight of the total amount of polyols in the gelled emulsion. Preferably the polyols contain a mixture of xylitol and sorbitol, where the weight ratio of xylitol to sorbitol is 1.0-3.0, more preferably 1.2-2.8, still more preferably 1.5-2.5, and most preferably 1.7-2.2. Preferably the weight ratio of plant sterol ester and/or plant stanol ester to the total amount of polyols is at least 1.0, more preferably at least 1.4, still more preferably at least 1.7, even more preferably at least 2.0, further more preferably at least 2.5, and most preferably at least 3.0. Preferably the total amount of cariogenic sugars is at most 20%, more preferably at most 15%, still more preferably at most 10%, even more preferably at most 5.0% and further more preferably 0-0.1% by weight of the gelled emulsion. Most preferably there are no cariogenic sugars present in the gelled emulsion. Preferably the total amount of the acids and/or buffering agents is less than 15%, more preferably less than 13%, still more preferably less than 10%, even more preferably less than 8% and most preferably less than 6% by weight of the gelled emulsion. The daily dose of the gelled emulsion of this embodiment is preferably 1.0-25 g, more preferably 1.3-20 g, still more preferably 1.5-17 g, even more preferably 1.8-15 g, and most preferably 2.0-13 g. The size of the dose unit of the gelled emulsion is preferably 0.3-12.5 g, more preferably 0.4-10 g, still more preferably 0.5-9.0 g, even more preferably 0.6-8.0 g, further more preferably 0.7-7.0 g and most preferably 1.0-6.0 g. Preferably the energy content of the gelled emulsion is at most 840 kJ, more preferably at most 670 kJ, still more preferably at most 500 kJ, even more preferably at most 330 kJ and most preferably at most 200 kJ per daily dose of the gelled emulsion. The energy content per gram of the gelled emulsion is preferably at most 40 kJ, more preferably at most 35 kJ, still more preferably at most 30 kJ, even more preferably at most 25 kJ and most preferably at most 20 kJ. Preferably the gelled emulsion of this embodiment is uncoated.

The content of the plant sterol ester and/or plant stanol ester of the dietary supplement product can e.g. be analyzed by a method described by Lubinus et al. (Eur. J. Nutr. 2013, 52(3):997-1013) or by Esche et al. (J. Agric. Food Chem. 2012, 30; 60(21):5330-9). The water activity (aw) can be analyzed by using an instrument which measures the relative humidity of a sample, such as Novasina ms1 aw-meter.

In this description the amounts given in percentages mean percentage by weight (wt-%) of the gelled emulsion unless otherwise stated.

Comprising means "containing at least" in this context.

The invention will be described in greater detail by means of the following non-limiting examples.

Example 1

Gelled emulsions containing plant sterols and/or plant stanols were prepared. The targeted daily dose of the gelled emulsion was chosen to be 6.5 g. The targeted amount of plant sterols and/or plant stanols to be incorporated in the daily dose of the gelled emulsion was 2 g as sterol/stanol equivalents, which corresponds to 3.4 g as plant sterol ester and/or plant stanol ester or to 2 g as free plant sterols or stanols.

Three gelled emulsions were prepared (recipes 1a-1c). One of them was a reference product without plant sterols or plant stanols (1a), one was prepared with free plant sterols (1b) and one with plant stanol ester (1c). Some rapeseed oil was added to the recipe 1b in order to get the same content of rapeseed oil fatty acids as in the recipe 1c (corresponding the fatty acids of the plant stanol ester).

|  | 1a Comparative | 1b Comparative | 1c Invention |
|---|---|---|---|
| Plant stanol ester ingredient* | — | — | 53 |
| Rapeseed oil | 53 | 22 | — |
| Phytosterol powder (free sterols) |  | 31 |  |
| Water phase: |  |  |  |
| Water | 17.5 | 17.5 | 17.5 |
| Glycerol | 17 | 17 | 17 |
| Gelatin | 6.5 | 6.5 | 6.5 |
| Trisodium citrate | 4 | 4 | 4 |
| Citric acid | 1.6 | 1.6 | 1.6 |
| Orange flavor | 0.4 | 0.4 | 0.4 |

*containing 98% by weight plant stanol ester, i.e. plant stanol ester concentration in the recipe is 52% by weight; esterified with fatty acids from rapeseed oil; Raisio Nutrition Ltd Preparation Method:

The water phase was prepared first. Fish gelatin having a Bloom value 193 and low or medium viscosity (below 4.2 mPas) was used. Gelatin was added to the water and let to swell for 30 minutes. The gelatin solution was then heated to 70° C. with stirring and stirred at that temperature for 15 minutes. Other water soluble components were added (first glycerol, then citric acid and trisodium citrate), and allowed to dissolve under stirring for 30-60 minutes. Then the stirring was stopped and the blend was degassed and the mixture was allowed to cool for about 30 minutes (to about 55° C.).

1A: Rapeseed oil was warmed to 55° C., mixed with the flavor and emulsified with the water phase, by slowly adding it to the water phase and emulsifying by using an UltraTurrax (10000 rpm). The viscosity of the emulsion was measured at 55° C. (Brookfield viscometer, 1.5 rpm). The resulting emulsion was poured into moulds and let to gel for 60 minutes at room temperature (22° C.).

1B: The finely grounded phytosterol powder was mixed with rapeseed oil preheated at 100° C. The resulting mixture was very thick and the sterol did not completely dissolve in the oil. The flavor was added into this mixture. The mixture was slowly added and mixed with the water phase, by using an UltraTurrax (10000 rpm), but it could not be evenly dispersed in the water phase. The resulting inhomogeneous mixture was placed into moulds, and let to stay there for 5 hours at room temperature (22° C.). The mixture did not gel.

1C: Plant stanol ester was heated until totally melted, the flavor was added and then the mixture was slowly added to the water phase and emulsified with the water phase at 55° C., by using an UltraTurrax (10000 rpm). The viscosity of the emulsion was measured at 55° C. (Brookfield viscometer, 1.5 rpm). The resulting emulsion was poured into moulds and let to gel for 60 minutes at room temperature (22° C.).

The resulting products were evaluated by a trained sensory panel. Results are presented in the table below.

|  | 1a | 1b | 1c |
|---|---|---|---|
| Properties of the emulsion | Emulsion is well flowing, pourable. Viscosity at 55° C. 5500 mPas. | The sterol-rapeseed oil mixture was too thick, and could not be evenly dispersed in the water phase. The product did not gel. | Emulsion is stable and pourable, there is no phase separation. Viscosity at 55° C. 11000 mPas. |
| Appearance, Texture, Mouthfeel | Oily surface, oily mouthfeel, the gel does not seem to retain the oil, too soft product | The product could not be prepared | Soft, but still good texture, chewable, not gummy, not sticky, no oily surface, no oily mouthfeel, pleasant |
| Taste | Mild orange taste. Oily taste, especially oily aftertaste. | The product could not be prepared | Mild orange taste, no oily or fatty taste, no aftertaste |

The gelled emulsion prepared with plant stanol ester (1c) was found to be stable and to have acceptable viscosity before gelling. The final product, i.e. the gelled emulsion, had soft, chewable texture, which was not gummy. There was no oily or fatty mouthfeel. The recipe provided 3.4 g plant stanol ester in 6.5 g of the gelled emulsion (dose unit size 6.5 g), which is a very convenient daily dose. The weight ratio of the plant stanol ester to the gelling agent (gelatin) in this recipe was 8.0. The recipe contained 17% glycerol. The weight ratio of the plant stanol ester to the total amount of polyols was 3.1. Despite the high content of plant stanol ester, the emulsion gelled well and had a good texture. The dose unit of the gelled emulsion was not coated, but it was used as an edible product, such as a dietary supplement product, as such.

It was not possible to prepare a gelled emulsion providing an equivalent amount of the cholesterol lowering plant sterol ingredient (2 g free plant sterols) in 6.5 g of the product (recipe 1b).

Example 2

Gelled Emulsion Containing 68% by Weight Plant Stanol Ester

|  | % |
|---|---|
| Plant stanol ester ingredient* | 69.3 |
| Water | 12.8 |
| Glycerol | 10.1 |

-continued

|  | % |
| --- | --- |
| Gelatin | 4.0 |
| Trisodium citrate | 1.5 |
| Malic acid 99% | 1.0 |
| Flavor | 0.7 |
| Color | 0.5 |
| Sweetener (stevia) | 0.1 |
|  | 100 |

*containing 98% by weight plant stanol ester, i.e. plant stanol ester concentration in the recipe 68% by weight. Plant stanols were esterified with rapeseed oil fatty acids The gelled emulsion was prepared in a similar way as described in the example 1c, except a lower shear rate was used in the emulsification step (Ultra Turrax 8000 rpm). The gelatin used had a bloom value of 255 and low or medium viscosity (at most 4.2 mPas). The color and the flavor were added into the plant stanol ester before emulsifying it with the water phase. The emulsion was thick, stable and gelled well. The gelled emulsion that was obtained had soft and chewable texture (a bit harder than the texture of the gelled emulsion in example 1c), which was not gummy. The mouthfeel was not fatty or oily. The recipe provided 3.4 g plant stanol ester in 5.0 g of the gelled emulsion. The weight ratio of the plant stanol ester to the gelling agent (gelatin) in this recipe was 17. The recipe contained 10.1% by weight glycerol. The weight ratio of the plant stanol ester to the total amount of polyols was 6.7.

Example 3

Gelled Emulsion Containing 50% by Weight of Plant Stanol Ester and Plant Sterol Ester

|  | % |
| --- | --- |
| Plant stanol ester ingredient* | 40.8 |
| Plant sterol ester ingredient** | 10.3 |
| Water | 18.2 |
| Gelatin | 6.2 |
| Glycerol | 10.0 |
| Sorbitol | 1.4 |
| Xylitol | 6.7 |
| Malic acid 99% | 1.8 |
| Trisodium Citrate | 3.6 |
| Flavor | 1.0 |
| Color | .03 |
|  | 100.0 |

*containing 98% by weight plant stanol ester (the same as in 1c)
**containing 97.5% by weight plant sterol ester, both esterified with rapeseed oil fatty acids. The plant stanol ester and plant sterol ester concentration in the recipe was 50% by weight.

The gelled emulsion was prepared in a similar way as described in the example 1c. Plant stanol ester and plant sterol ester were melted and mixed before emulsification with the water phase. The gelatin used had a bloom value of 160. The emulsion was stable and gelled well upon cooling. The texture of the gelled emulsion obtained was homogeneous and chewable, although a bit harder than the texture of the gelled emulsion in example 1c. The texture was not gummy and the mouthfeel was good (not fatty or oily). The recipe provided 3.4 g plant stanol ester and plant sterol ester in 6.8 g of the gelled emulsion. The weight ratio of the plant stanol ester and plant sterol ester to the gelling agent (gelatin) in this recipe was 8.1. The recipe contained 10.0% by weight glycerol and 6.7% by weight xylitol, and the amount of glycerol was 55.2% and the amount of xylitol 37.0% by weight of the total amount of polyols. The weight ratio of the plant stanol ester and plant sterol ester to the total amount of polyols was 2.8.

Example 4

Gelled Emulsion Containing 42% by Weight of Plant Stanol Ester

|  | % |
| --- | --- |
| Plant stanol ester ingredient* | 43.0 |
| Water | 18.6 |
| Xylitol | 3.6 |
| Glycerol | 21.0 |
| Gelatin | 6.5 |
| Trisodium citrate | 3.6 |
| Malic acid 99% | 1.8 |
| Flavor | 1.0 |
| Color | 0.7 |
| Sweetener | 0.2 |
|  | 100 |

*containing 98% by weight plant stanol ester (the same as in 1c), i.e. plant stanol ester concentration in the recipe 42% by weight The gelled emulsion was prepared in a similar way as described in the example 1c. The gelatin used had a bloom value of 260, and low or medium viscosity (at most 4.2 mPas). The emulsion was stable, well flowing and fairly thin, but gelled well upon cooling. The gelled emulsion obtained had soft (softer than the gelled emulsion in the example 1c), chewable and homogeneous texture. The texture was not gummy. The mouthfeel was good, not fatty or oily. The recipe provided 3.4 g plant stanol ester in 8.1 g of the gelled emulsion. The weight ratio of the plant stanol ester to the gelling agent (gelatin) in this recipe was 6.5. The recipe contained 21.0% by weight glycerol, and the amount of glycerol was 85.4% by weight of the total amount of polyols. The recipe contained 3.6% xylitol and the amount of xylitol was 14.6% of the total polyols. The weight ratio of plant stanol ester to the total amount of polyols was 1.7.

Example 5

Gelled Emulsion, Containing 59% of Plant Stanol Ester

|  | % |
| --- | --- |
| Plant stanol ester ingredient* | 60.0 |
| Water | 16.8 |
| Xylitol | 7.2 |
| Glycerol | 7.2 |
| Gelatin | 5.0 |
| Trisodium citrate | 1.8 |
| Citric acid | 0.5 |
| Flavor | 0.9 |
| Color | 0.5 |
| Sweetener | 0.1 |
|  | 100 |

*containing 98% by weight plant stanol ester (the same as in 1c), i.e. plant stanol ester concentration in the recipe 59% by weight The gelled emulsion was prepared in a similar way as described in the example 1c, except a lower shear rate was used in the emulsification step (Ultra Turrax 8000 rpm). The gelatin used had a bloom value of 255, and low or medium viscosity (at most 4.2 mPas). The emulsion was stable, fairly thick, but still pourable and gelled in moulds well upon cooling. The gelled emulsion obtained had soft, but firm texture, which was chewable. Also the mouthfeel was good, not fatty or oily. There was no gumminess either. The recipe provided 3.4 g plant stanol ester in 5.8 g of the gelled emulsion. The weight ratio of the plant stanol ester to the gelling agent (gelatin) in this recipe was 12. The recipe contained 7.2% by weight glycerol, and the amount of glycerol was 50% by weight of the total amount of polyols. The recipe contained also 7.2% by weight xylitol, and the amount of xylitol was 50% by weight of the total amount of polyols. The weight ratio of plant stanol ester to the total amount of polyols was 4.1.

Example 6

Packed Gelled Emulsion Containing 51% by Weight of Plant Stanol Ester

|   | % |
| --- | --- |
| Plant stanol ester ingredient* | 52.0 |
| Water | 16.2 |
| Xylitol | 19.8 |
| Glycerol | 3.7 |
| Gelatin | 4.5 |
| Trisodium citrate | 2.0 |
| Malic acid 99% | 0.7 |
| Flavor | 1.0 |
| Color | 0.1 |
|   | 100 |

*containing 98% by weight plant stanol ester (the same as in example 1c), i.e. plant stanol ester concentration in the recipe 51% by weight The gelled emulsion was prepared in a similar way as described in the example 1c, except a lower shear rate was used in the emulsification step (Ultra Turrax 6500 rpm). The gelatin used was bovine gelatin, having bloom value of 195. Of the polyols, xylitol was added first to the gelatin solution and stirred for 15 minutes. Glycerol was then added and the solution was stirred for additional 5 minutes, after which malic acid, trisodium citrate and the sweetener were added and the stirring continued for additional 20 minutes. Color and flavor were added into the plant stanol ester before its emulsification with the water phase. The emulsion was stable. 6.7 g of the emulsion was dosed into each dose unit mould (blister trays) and sealed with an aluminum foil. The dose units of the emulsion were allowed to cool in the blister pack and the emulsion gelled well upon cooling. The gelled emulsion had chewable, soft texture. The mouthfeel was pleasant, not fatty, oily or gummy-like. The recipe provided 3.4 g plant stanol ester in 6.7 g of the gelled emulsion. The weight ratio of the plant stanol ester to the gelling agent (gelatin) in this recipe was 11.3. The recipe contained 3.7% by weight glycerol, which was 15.7% by weight of the total amount of polyols (glycerol and xylitol). The recipe contained 19.8% by weight xylitol, which was 84.3% by weight of the total amount of polyols (glycerol and xylitol). The weight ratio of xylitol to glycerol was 5.4. The weight ratio of plant stanol ester to the total amount of polyols was 2.2.

Example 7

Gelled Emulsion Containing 47% by Weight of Plant Sterol Ester

|   | % |
| --- | --- |
| Plant sterol ester ingredient* | 48.2 |
| Water | 16.8 |
| Xylitol | 14.5 |
| Sorbitol | 7.2 |
| Glycerol | 4.0 |
| Gelatin | 5.4 |
| Trisodium citrate | 2.0 |
| Malic acid 99% | 0.7 |
| Flavor | 1.0 |
| Color | 0.1 |
|   | 100 |

*containing 97.5% by weight plant sterol ester (the same as in example 3), i.e. plant sterol ester concentration in the recipe 47% by weight The gelled emulsion was prepared in a similar way as described in the example 1c. The gelatin used was bovine gelatin, having a bloom value of 195, and low or medium viscosity. Of the polyols, sorbitol was added first to the gelatin solution and stirred for 5 minutes. Xylitol was added then and stirred for additional 10 minutes, after which glycerol was added and the stirring continued for additional 5 minutes. Malic acid and trisodium citrate were added then and the stirring continued for additional 20 minutes. Color and flavor were added into the plant sterol ester before its emulsification with the water phase. The emulsion gelled in moulds well upon cooling. The gelled emulsion had a bit harder surface than the gelled emulsions prepared with plant stanol ester. However, the inner texture was soft and the overall acceptability of the texture was still good, despite the bit harder surface. The mouthfeel was pleasant, not fatty or oily. The recipe provided 3.4 g plant sterol ester in 7.2 g of the gelled emulsion. The weight ratio of the plant sterol ester to the gelling agent (gelatin) in this recipe was 8.7. The recipe contained 4.0% by weight glycerol, which was 15.6% by weight of the total amount of polyols. The recipe contained also xylitol (14.5% by weight of the gelled emulsion and 56.4% by weight of the total amount of polyols), and sorbitol (7.2% by weight of the gelled emulsion and 28.0% by weight of the total amount of polyols). The weight ratio of xylitol to sorbitol was 2.0. The weight ratio of plant sterol ester to the total amount of polyols was 1.8.

Example 8

Gelled Emulsion Containing 54% by Weight of Plant Stanol Ester

|   | % |
| --- | --- |
| Plant stanol ester ingredient* | 55.0 |
| Water (purified) | 19.2 |
| Xylitol | 8.8 |
| Sorbitol | 4.0 |
| Gelatin | 6.0 |
| Trisodium citrate | 3.6 |
| Malic acid 99% | 1.8 |
| Flavor (lemon) | 1.0 |
| Color | 0.6 |
|   | 100 |

*containing 98% by weight plant stanol ester (the same as in 1c), i.e. plant stanol ester concentration in the recipe 54% by weight The gelled emulsion was prepared in a similar way as described in the example 1c, except a lower shear rate was used in the emulsification step (Ultra Turrax 6500 rpm). The gelatin used was bovine gelatin having bloom value of 150, and low or medium viscosity. The emulsion was stable and gelled in moulds well upon cooling. The gelled emulsion obtained had chewable and soft texture, and good lemon taste. The mouthfeel was not fatty or oily. There was no gumminess either. The recipe provided 3.4 g plant stanol ester in 6.3 g of the gelled emulsion. The weight ratio of the plant stanol ester to the gelling agent (gelatin) in this recipe was 9. The recipe contained 8.8% by weight xylitol, and the amount of xylitol was 69% by weight of the total amount of polyols. The weight ratio of xylitol to sorbitol was 2.2. The weight ratio of plant stanol ester to the total amount of polyols was 4.2.

Example 9

Gelled Emulsion Containing 40% by Weight of Plant Stanol Ester

|  | % |
|---|---|
| Plant stanol ester ingredient* | 41.0 |
| Water | 18.3 |
| Xylitol | 18.2 |
| Sorbitol | 9.4 |
| Gelatin | 6.2 |
| Trisodium citrate | 3.6 |
| Malic acid 99% | 1.8 |
| Flavor | 0.8 |
| Color | 0.7 |
|  | 100 |

*containing 98% by weight plant stanol ester (the same as in example 1c), i.e. plant stanol ester concentration in the recipe 40% by weight The gelled emulsion was prepared in a similar way as described in the example 1c, except a bit higher shear rate was used in the emulsification step (Ultra Turrax 11500 rpm). The gelatin used was bovine gelatin, having bloom value of 150, and low or medium viscosity. The emulsion was stable and gelled well upon cooling. The gelled emulsion obtained had soft, but firm texture, which was chewable. The mouthfeel was good, not fatty, oily or gummy-like. The recipe provided 3.4 g plant stanol ester in 8.5 g of the gelled emulsion. The weight ratio of the plant stanol ester to the gelling agent (gelatin) in this recipe was 6.5. The recipe contained 18.2% by weight xylitol, and the amount of xylitol was 66% by weight of the total amount of polyols. The weight ratio of xylitol to sorbitol was 1.9. The weight ratio of plant stanol ester to the total amount of polyols was 1.4.

Example 10

Gelled Emulsion Containing 44% by Weight of Plant Sterol Ester

|  | % |
|---|---|
| Plant sterol ester ingredient* | 45.0 |
| Water | 18.3 |
| Xylitol | 15.0 |
| Sorbitol | 8.6 |
| Gelatin | 6.2 |
| Trisodium citrate | 3.6 |
| Malic acid | 1.8 |
| Flavor | 1.0 |
| Color | 0.5 |
|  | 100 |

*containing 97.5% by weight plant sterol ester (the same as in example 3), i.e. plant sterol ester concentration in the recipe 44% by weight The gelled emulsion was prepared in a similar way as described in the example 1c, except a bit higher shear rate was used in the emulsification step (Ultra Turrax 11000 rpm). The gelatin used was bovine gelatin having a bloom value of 160, and low or medium viscosity. The emulsion was stable and gelled in moulds well upon cooling. The gelled emulsion obtained had a harder surface texture than the gelled emulsions prepared with plant stanol ester, but the inner texture was still good, chewable and soft. The mouthfeel was not fatty or oily. The recipe provided 3.4 g plant sterol ester in 7.7 g of the gelled emulsion. The weight ratio of the plant sterol ester to the gelling agent in this recipe was 7.1. The recipe contained 15.0% by weight xylitol, and the amount of xylitol was 63.6% by weight of the total amount of polyols. The weight ratio of xylitol to sorbitol was 1.7. The weight ratio of plant sterol ester to the total amount of polyols was 1.9.

Example 11

Gelled Emulsion Containing 54% by Weight of Plant Stanol Ester

|  | % |
|---|---|
| Plant stanol ester ingredient* | 55.0 |
| Water | 18.0 |
| Erythritol | 6.6 |
| Xylitol | 6.6 |
| Sorbitol | 1.4 |
| Gelatin | 5.8 |
| Trisodium citrate | 3.6 |
| Malic acid 99% | 1.8 |
| Flavor | 0.5 |
| Color | 0.7 |
|  | 100 |

*containing 98% by weight plant stanol ester (the same as in example 1c), i.e. plant stanol ester concentration in the recipe 54% by weight The gelled emulsion was prepared in a similar way as described in the example 1c. The gelatin used was bovine gelatin, having bloom value of 240-260, and low or medium viscosity (at most 4.2 mPas). The emulsion was stable and gelled well upon cooling. The gelled emulsion obtained had soft and chewable texture. The mouthfeel was good, not fatty or oily and it was not gummy-like. The recipe provided 3.4 g plant stanol ester in 6.3 g of the gelled emulsion. The weight ratio of the plant stanol ester to the gelling agent (gelatin) in this recipe was 9.3. The recipe contained 6.6% by weight xylitol, which was 45% by weight of the total amount of xylitol, sorbitol and erythritol. The weight ratio of plant stanol ester to the total amount of polyols was 3.7.

Further Embodiments of the Invention

1. A gelled emulsion comprising
    plant sterol ester and/or plant stanol ester in an amount of at least 20% by weight,
    gelling agent in an amount of at most 15% by weight, and
    water in an amount of 3.0-35% by weight.
2. The gelled emulsion according to embodiment 1, characterised in that the amount of plant sterol ester and/or plant stanol ester is at most 80%, preferably at most 75%, more preferably at most 73%, still more preferably at most 70% and most preferably at most 68% by weight.
3. The gelled emulsion according to embodiment 1 or 2, characterised in that the amount of plant sterol ester and/or plant stanol ester is at least 25%, preferably at least 30%, more preferably at least 35%, still more preferably at least 40%, even more preferably at least 42%, further more preferably at least 45%, still further more preferably at least 48%, even further more preferably at least 50% and most preferably at least 52% by weight.

4. The gelled emulsion according to any one of embodiments 1 to 3, characterised in that the plant sterol ester and/or plant stanol ester comprises plant stanol ester in an amount of at least 10%, preferably at least 50%, more preferably at least 70% and most preferably at least 90% by weight.

5. The gelled emulsion according to any one of embodiments 1 to 4, characterised in that the gelled emulsion further comprises triglyceride fat in an amount of 0-20%, preferably 0-15%, more preferably 0-10%, still more preferably 0-9.0%, even more preferably 0-8.0%, further more preferably 0-6.0%, still further more preferably 0-4.0%, still even further more preferably 0-2.0% and most preferably 0-0.1% by weight.

6. The gelled emulsion according to any one of embodiments 1 to 5, characterised in that the total amount of the gelling agent is at most 14%, preferably at most 13%, more preferably at most 12%, still more preferably at most 11% and most preferably at most 10% by weight.

7. The gelled emulsion according to any one of embodiments 1 to 6, characterised in that the total amount of the gelling agent is at least 0.1%, preferably at least 0.2%, more preferably at least 0.3%, still more preferably at least 0.4% and most preferably at least 0.5% by weight.

8. The gelled emulsion according to any one of embodiments 1 to 7, characterised in that the gelling agent is selected from the group consisting of one or more proteins, one or more polysaccharides and any mixture thereof, preferably from the group consisting of gelatin, carrageenan, pectin, alginate, gellan gum, agar, starch, starch derivatives, gum Arabic, inulin, xanthan gum, locust bean gum, glucomannan and/or mixtures thereof, more preferably from the group consisting of gelatin, carrageenan, pectin, alginate, gellan gum, agar, starch, starch derivatives, and polymer compounds which form gels when used together with other polymer compounds such as xanthan gum and locust bean gum; xanthan gum and glucomannan; inulin and any one of gelatin, gellan gum, carrageenan or pectin, and mixtures thereof, still more preferably from the group consisting of gelatin, carrageenan, pectin, alginate, gellan gum, agar or mixtures thereof.

9. The gelled emulsion according to any one of embodiments 1 to 8, characterised in that the gelling agent comprises gelatin, preferably in an amount of at least 50% more preferably at least 60%, still more preferably at least 70%, even more preferably at least 80% and most preferably at least 90% by weight, and optionally at least one gelling agent selected from the group consisting of carrageenan, pectin, alginate, gellan gum and agar, and most preferably the gelling agent is gelatin.

10. The gelled emulsion according to embodiment 9, characterised in that the amount of gelatin is 1.0-15%, preferably 2.0-14%, more preferably 2.5-13%, still more preferably 3.0-12%, even more preferably 3.5-11% and most preferably 4.0-10% by weight.

11. The gelled emulsion according to embodiment 9 or 10, characterised in that the amount of gelatin is 15-55%, preferably 20-50%, more preferably 22-45% and most preferably 25-40% by weight of the amount of water in the gelled emulsion.

12. The gelled emulsion according to any one of embodiments 1 to 11, characterised in that the gelled emulsion further comprises one or more polyols.

13. The gelled emulsion according to embodiment 12, characterised in that the total amount of polyols is 1.0-60%, preferably 1.0-50%, more preferably 2.0-50%, still more preferably 3.0-40%, even more preferably 4.0-35%, further more preferably 4.0-30%, still further more preferably 5.0-30%, even further more preferably 5.0-25% and most preferably 5.0-20% by weight.

14. The gelled emulsion according to embodiment 12 or 13, characterised in that the polyols comprise glycerol, and preferably the amount of glycerol is at least 5%, more preferably at least 10%, still more preferably at least 15%, even more preferably at least 20%, further more preferably at least 50%, still further more preferably at least 70% and most preferably at least 85% by weight of the total amount of polyols.

15. The gelled emulsion according to embodiment 12 or 13, characterised in that the polyols comprise xylitol, and preferably the amount of xylitol is at least 5%, more preferably at least 10%, still more preferably at least 20%, even more preferably at least 40%, further more preferably at least 50%, still further more preferably at least 60%, even further more preferably at least 65% and most preferably at least 80% by weight of the total amount of polyols.

16. The gelled emulsion according to embodiment 12 or 13, characterised in that the polyols comprise glycerol and xylitol, and preferably the weight ratio of glycerol to xylitol is 0.05-10, more preferably 0.08-2.0, still more preferably 0.11-1.0, even more preferably 0.14-0.8, and most preferably 0.16-0.5, and/or the amount of glycerol is preferably at least 5%, more preferably at least 7%, still more preferably at least 10%, even more preferably at least 12% and most preferably at least 14% by weight of the total amount of glycerol and xylitol.

17. The gelled emulsion according to embodiment 12 or 13, characterised in that the polyols comprise xylitol and sorbitol, and preferably the weight ratio of xylitol to sorbitol is 1.0-3.0, more preferably 1.2-2.8, still more preferably 1.5-2.5 and most preferably 1.7-2.2.

18. The gelled emulsion according to embodiment 12 or 13, characterised in that the polyols comprise glycerol, xylitol and sorbitol, and preferably the weight ratio of glycerol to the total amount of xylitol and sorbitol is 0.05-10, more preferably 0.08-2.0, still more preferably 0.11-1.0, even more preferably 0.14-0.8, and most preferably 0.16-0.5, and/or the weight ratio of xylitol to sorbitol is preferably 1.0-3.0, more preferably 1.2-2.8, still more preferably 1.5-2.5, and most preferably 1.7-2.2 and/or the amount of glycerol is preferably at least 5%, more preferably at least 7%, still more preferably at least 10%, even more preferably at least 12%, and most preferably at least 14% by weight of the total amount of glycerol, xylitol and sorbitol.

19. The gelled emulsion according to any one of embodiments 1 to 18, characterised in that it further comprises one or more cariogenic sugars selected from the group consisting of sucrose, glucose, fructose, maltose and lactose.

20. The gelled emulsion according to embodiment 19, characterised in that the total amount of cariogenic sugars is at most 20%, preferably at most 15%, more preferably at most 10%, still more preferably at most 5%, even more preferably 0-0.1% by weight.

21. The gelled emulsion according to any one of embodiments 1 to 18, characterised in that there are no cariogenic sugars present in the gelled emulsion.

22. The gelled emulsion according to any one of embodiments 1 to 21, characterised in that the weight ratio of the plant sterol ester and/or plant stanol ester to the gelling agent is at least 6.0, preferably at least 6.5, more preferably at least 7.0, still more preferably at least 7.5 and most preferably at least 8.0.

23. The gelled emulsion according to any one of embodiments 6 to 22, characterised in that the weight ratio of the plant sterol ester and/or plant stanol ester to the triglyceride fat is at least 1.3, preferably at least 1.5, more preferably at least 2.0, still more preferably at least 3.0, even more preferably at least 4.0, further more preferably at least 5.0, still further more preferably at least 6.0 and most preferably at least 13.

24. The gelled emulsion according to any one of embodiments 12 to 23, characterised in that the weight ratio of plant sterol ester and/or plant stanol ester to the total amount of polyols is at least 1.0, preferably at least 1.4, more preferably at least 1.7, still more preferably at least 2.0, even more preferably at least 2.5 and most preferably at least 3.0.

25. The gelled emulsion according to any one embodiments 1 to 24, characterised in that the size of the dose unit of the gelled emulsion is at least 0.3 g, preferably 0.3-12.5 g, more preferably 0.4-10 g, still more preferably 0.5-9.0 g, even more preferably 0.6-8.0 g, further more preferably 0.7-7.0 g and most preferably 1.0-6.0 g.

26. The gelled emulsion according to any one of embodiments 1 to 25, characterised in that the daily dose of the gelled emulsion is 1.0-25 g, preferably 1.3-20 g, more preferably 1.5-17 g, still more preferably 1.8-15 g and most preferably 2.0-13 g.

27. The gelled emulsion according to any one of embodiments 1 to 26, characterised in that its water activity aw is at most 0.90, preferably at most 0.87, more preferably at most 0.85, still more preferably at most 0.80 and most preferably at most 0.75.

28. The gelled emulsion according to any one of embodiments 1 to 27, characterised in that its water content is 4.0-34%, preferably 5.0-33%, more preferably 6.0-32%, still more preferably 7.0-31%, even more preferably 8.0-30%, further more preferably 9.0-29%, still further more preferably 10-28% and most preferably 11-27% by weight.

29. The gelled emulsion according to any one of embodiments 1 to 28, characterised in that it further comprises pH modifiers, such as acids and buffering agents, preferably the total amount of the acids and/or buffering agents is less than 15%, more preferably less than 13%, still more preferably less than 10%, even more preferably less than 8.0% and most preferably less than 6.0% by weight.

30. The gelled emulsion according to any one of embodiments 1 to 29, characterised in that its energy content is at most 840 kJ, preferably at most 670 kJ, more preferably at most 500 kJ, still more preferably at most 330 kJ and most preferably at most 200 kJ per daily dose of the gelled emulsion.

31. The gelled emulsion according to any one of embodiments 1 to 30, characterised in that its energy content per gram of the gelled emulsion is at most 40 kJ, preferably at most 35 kJ, more preferably at most 30 kJ, still more preferably at most 25 kJ and most preferably at most 20 kJ.

32. The gelled emulsion according to any one of embodiments 1 to 31, characterised in that it is a solid gelled emulsion and/or it is solid at 20° C., preferably at 22° C., more preferably at 25° C. and most preferably at 30° C. and/or it is chewable and/or it can be stored at room temperature.

33. The gelled emulsion according to any one of embodiments 1 to 32, characterised in that it is a dietary supplement product.

34. The gelled emulsion according to any one of embodiments 1 to 33, characterised in that it comprises
plant sterol ester and/or plant stanol ester in an amount of 25-80% by weight,
gelling agent in an amount of at most 13% by weight,
water in an amount of 5.0-33% by weight, and the water activity of the gelled emulsion being at most 0.80
optionally triglyceride fat in an amount of 0-20% by weight, and
optionally polyol(s) in an amount of 1.0-50% by weight.

35. The gelled emulsion according to embodiment 34, characterised in that it comprises one or more polyols in a total amount of 1.0 to 50% preferably 2.0-50%, more preferably 3.0-40%, still more preferably 4.0-35%, even more preferably 4.0-30%, further more preferably 5.0-30%, still further more preferably 5.0-25% and most preferably 5.0-20% by weight.

36. The gelled emulsion according to embodiment 34 or 35, characterised in that it comprises
plant sterol ester and/or plant stanol ester in an amount of 35-75% by weight,
gelling agent in an amount of at most 12% by weight.

37. The gelled emulsion according to embodiment 36, characterised in that the weight ratio of the plant sterol ester and/or plant stanol ester to the triglyceride fat is at least 2.0, preferably at least 3.0, more preferably at least 4.0, still more preferably at least 5.0, even more preferably at least 6.0 and most preferably at least 13.

38. The gelled emulsion according to embodiment 34, characterised in that it comprises
plant sterol ester and/or plant stanol ester in an amount of 40-75% by weight,
gelling agent in an amount of at most 12% by weight,
water in an amount of 6.0-32% by weight,
optionally triglyceride fat in an amount of 0-10% by weight, and
optionally polyol(s) in an amount of 1.0-40% by weight.

39. The gelled emulsion according to embodiment 38, characterised in that the weight ratio of the plant sterol ester and/or plant stanol ester to the triglyceride fat is at least 5.0, preferably at least 6.0 and most preferably at least 13.

40. The gelled emulsion according to embodiment 38 or 39, characterised in that it comprises one or more polyols in a total amount of 1.0-40%, preferably 2.0-40%, more preferably 3.0-40%, still more preferably 4.0-35%, even more preferably 5.0-30, further more preferably 5.0-25% and most preferably 5.0-20% by weight.

41. The gelled emulsion according to any one of embodiments 38 to 40, characterised in that it comprises
plant sterol ester and/or plant stanol ester in an amount of 45-73% by weight,
gelling agent in an amount of at most 12% by weight,
water in an amount of 7.0-31% by weight,
optionally triglyceride fat in an amount of 0-9.0% by weight, and
optionally polyol(s) in an amount of 1.0-40% by weight.

42. The gelled emulsion according to embodiment 41, characterised in that the weight ratio of the plant sterol ester and/or plant stanol ester to the triglyceride fat is at least 6.0 and most preferably at least 13.

43. The gelled emulsion according to any one of embodiments 34 to 42, characterised in that it contains no cariogenic sugar.

44. The gelled emulsion according to any one of embodiments 34 to 43, characterised in that the weight ratio of the plant sterol ester and/or plant stanol ester to the gelling agent is at least 6.0, preferably at least 6.5, more preferably at least 7.0, still more preferably at least 7.5 and most preferably at least 8.0.

45. The gelled emulsion according to any one of embodiments 34 to 44, characterised in that the gelling agent comprises gelatin and preferably is gelatin.

46. The gelled emulsion according to embodiment 45, characterised in that the amount of gelatin is 15-55%, preferably 20-50%, more preferably 22-45% and most preferably 25-40% by weight of the amount of water in the gelled emulsion.

47. The gelled emulsion according to embodiment 45 or 46, characterised in that the amount of gelatin is 3.0-12%, preferably 3.5-11% and most preferably 4.0-10% by weight of the gelled emulsion.

48. The gelled emulsion according to any one of embodiments 34-47, characterised in that the polyols comprise glycerol, and preferably the amount of glycerol is at least 5%, more preferably at least 10%, still more preferably at least 15%, even more preferably at least 20%, further more preferably at least 50%, still further more preferably at least 70% and most preferably at least 85% by weight of the total amount of polyols.

49. The gelled emulsion according to any one of embodiments 34-48, characterised in that the amount of water is 8.0-30%, preferably 9.0-29%, more preferably 10-28% and most preferably 11-27% by weight.

49B. The gelled emulsion according to any one of embodiments 1 to 49, characterised in that it comprises plant sterol ester and/or plant stanol ester in an amount of 40-75% by weight, gelatin in an amount of 3.0-12% by weight, water in an amount of 11-27% by weight, one or more polyols in a total amount of 5.0-25% by weight, and optionally triglycerides in an amount of 0 to 2.0% by weight, wherein the water activity $a_w$ of the gelled emulsion is at most 0.80 and the weight ratio of plant sterol ester and/or plant stanol ester to gelatin is at least 6.0, and preferably the amount of gelatin is 22-45% by weight of the amount of water in the gelled emulsion.

50. Use of the gelled emulsion according to any one of embodiments 1 to 49B for preparing an edible product.

51. An edible product comprising the gelled emulsion according to any one of embodiments 1 to 49B.

52. The edible product according to embodiment 51, characterised in that it is a dietary supplement.

53. The edible product according to embodiment 51 or 52, characterised in that it further comprises a coating.

54. The edible product according to embodiment 51 or 52, characterised in that it is uncoated.

55. The edible product according to any one of embodiments 51 to 54, characterised in that it is packed in a blister.

56. The edible product according to any one of embodiments 51 to 55, characterised in that it is portable and/or it is chewable and/or it can be stored at room temperatures and/or it has a long shelf life at room temperatures.

57. A blister comprising the gelled emulsion according to any one of embodiments 1 to 49B or the edible product according to any one of embodiments 51 to 56.

58. The gelled emulsion according to any one of embodiments 1 to 49B or the edible product according to any one of embodiments 51 to 56 for use as a medicament.

59. The gelled emulsion according to any one of embodiments 1 to 49B or the edible product according to any one of embodiments 51 to 56 for lowering serum LDL cholesterol level.

60. A method for preparing the gelled emulsion according to any one of embodiments 1 to 49B comprising
a) preparing an aqueous phase by mixing water and gelling agent, and optionally other water soluble ingredients, preferably at a temperature of at least 40° C.,
b) melting plant sterol ester and/or plant stanol ester, preferably at a temperature of at least 40° C., and optionally mixing it with other lipid soluble ingredients,
c) emulsifying the melted plant sterol ester and/or plant stanol ester, or the mixture of plant sterol ester and/or plant stanol ester and other lipid soluble ingredients, with the aqueous phase, preferably at a temperature of at least 40° C.,
d) feeding the obtained emulsion, preferably at a temperature of at least 40° C. into moulds, preferably into dose unit moulds, and
e) allowing the emulsion to cool to or below the gelation temperature of the aqueous phase to obtain the gelled emulsion.

61. A method for preparing the edible product according to any one of embodiments 51 to 56 comprising
a) preparing an aqueous phase by mixing water and gelling agent, and optionally other water soluble ingredients, preferably at a temperature of at least 40° C.,
b) melting plant sterol ester and/or plant stanol ester, preferably at a temperature of at least 40° C., and optionally mixing it with other lipid soluble ingredients,
c) emulsifying the melted plant sterol ester and/or plant stanol ester, or the mixture of plant sterol ester and/or plant stanol ester and other lipid soluble ingredients, with the aqueous phase, preferably at a temperature of at least 40° C.,
d) feeding the obtained emulsion, preferably at a temperature of at least 40° C. into dose unit moulds,
e) allowing the emulsion to cool to or below the gelation temperature of the aqueous phase to obtain a dose unit of the gelled emulsion,
f) optionally coating the dose unit,
g) packing the obtained dose unit.

62. The method according to embodiment 60 or 61, characterised in that step b is performed at a temperature of 40-80° C.

63. The method according to any one of embodiments 60 to 62, characterised in that step c is performed at a temperature of 40-80° C., preferably at 45-70° C. and most preferably at 45-60° C.

64. The method according to any one of embodiments 61 to 63, characterised in that the method includes no coating step f.

65. The method according to any one of embodiments 61 to 64, characterised in that the dose unit is packed in a blister.

The invention claimed is:
1. A gelled emulsion comprising:
plant sterol ester and/or plant stanol ester in an amount of 40-68% by weight;
at least one polyol selected from the group consisting of glycerol, xylitol, sorbitol, erythritol, and combinations thereof, in a total amount of 5-40% by weight;
gelatin as a gelling agent in an amount of 4-10% by weight; and
water in an amount of 11-27% by weight;

wherein the weight ratio of the plant sterol ester and/or plant stanol ester to the gelatin is at least 6.0:1; and wherein the gelled emulsion is solid at room temperature.

2. The gelled emulsion according to claim 1, wherein the gelled emulsion further comprises triglyceride fat in an amount of 0-20% by weight.

3. The gelled emulsion according to claim 1, wherein the polyol is glycerol and xylitol.

4. The gelled emulsion according to claim 1, wherein the polyol is xylitol and sorbitol.

5. The gelled emulsion according to claim 4, further comprising erythritol.

6. The gelled emulsion according to claim 1, wherein there are no cariogenic sugars present in the gelled emulsion.

7. The gelled emulsion according to claim 1, wherein the size of the dose unit of the gelled emulsion is at least 0.3 g.

8. The gelled emulsion according to claim 1, wherein water activity of the gelled emulsion is at most 0.90.

9. The gelled emulsion according to claim 1, wherein its energy content per gram of the gelled emulsion is at most 40 kJ.

10. The gelled emulsion according to claim 1, wherein it is a dietary supplement product.

11. An edible product comprising the gelled emulsion according to claim 1.

12. The edible product according to claim 11, wherein it is uncoated.

13. The edible product according to claim 11, wherein it is packed in a blister.

14. The gelled emulsion according to claim 10 for lowering serum LDL cholesterol level.

15. The edible product according to claim 11 for lowering serum LDL cholesterol level.

16. A method for preparing the edible product according to claim 11, comprising:
a) preparing an aqueous phase by mixing water, polyol and gelling agent at a temperature of at least 40° C.;
b) melting plant sterol ester and/or plant stanol ester at a temperature of at least 40° C.;
c) emulsifying the melted plant sterol ester and/or plant stanol ester with the aqueous phase at a temperature of at least 40° C.;
d) feeding the obtained emulsion at a temperature of at least 40° C. in dose unit moulds;
e) allowing the emulsion to cool to or below the gelation temperature of the aqueous phase to obtain a dose unit of the gelled emulsion;
f) optionally coating the dose unit; and
g) packing the obtained dose unit;
wherein the dose unit comprises:
plant sterol ester and/or plant stanol ester in an amount of 40-68% by weight;
at least one polyol selected from the group consisting of glycerol, xylitol, sorbitol, erythritol, and combinations thereof, in a total amount of 5-40% by weight;
gelatin as the gelling agent in an amount of 4-10% by weight; and
water in an amount of 11-27% by weight;
wherein the weight ratio of the plant sterol ester and/or plant stanol ester to the gelatin is at least 6.0:1; and
wherein the gelled emulsion is solid at room temperature.

17. The gelled emulsion according to claim 1, comprising:
52-68% by weight plant stanol ester;
4-10% by weight gelatin;
9-20% by weight glycerol; and
11-27% by weight water.

* * * * *